(12) United States Patent
Zurschmiede

(10) Patent No.: US 8,956,356 B2
(45) Date of Patent: Feb. 17, 2015

(54) TELESCOPING SCREW FOR FEMORAL NECK FRACTURES

(75) Inventor: Silas Zurschmiede, Oberdorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 225 days.

(21) Appl. No.: 13/462,544

(22) Filed: May 2, 2012

(65) Prior Publication Data
US 2013/0116694 A1 May 9, 2013

Related U.S. Application Data

(60) Provisional application No. 61/487,140, filed on May 17, 2011.

(51) Int. Cl.
*A61B 17/74* (2006.01)
*A61B 17/88* (2006.01)

(52) U.S. Cl.
CPC .............. *A61B 17/74* (2013.01); *A61B 17/8894* (2013.01); *A61B 17/742* (2013.01); *A61B 17/8872* (2013.01); *A61B 17/746* (2013.01)
USPC ........................................................ 606/65

(58) Field of Classification Search
CPC .... A61B 17/74; A61B 17/742; A61B 17/746; A61B 17/8872; A61B 17/8894
USPC ............... 606/63, 65, 68, 300, 301, 304, 306, 606/313, 314, 320, 104, 99, 86 A, 105
See application file for complete search history.

(56) References Cited

U.S. PATENT DOCUMENTS

| | | | |
|---|---|---|---|
| 2,397,545 A | 4/1946 | Hardinge | |
| 4,172,452 A | 10/1979 | Forte et al. | |
| 4,640,271 A | 2/1987 | Lower | |
| 4,940,467 A | 7/1990 | Tronzo | |
| 5,122,133 A | 6/1992 | Evans | |
| 5,498,265 A | 3/1996 | Asnis et al. | |
| 5,993,450 A | 11/1999 | Worcel | |
| 6,319,254 B1 | 11/2001 | Giet et al. | |
| 6,887,243 B2 * | 5/2005 | Culbert | 606/65 |
| 7,582,107 B2 | 9/2009 | Trail et al. | |
| 7,951,198 B2 | 5/2011 | Sucec et al. | |
| 2005/0245933 A1 | 11/2005 | Sevrain | |
| 2010/0036440 A1 | 2/2010 | Morris et al. | |
| 2011/0224738 A1 | 9/2011 | Sucec et al. | |

FOREIGN PATENT DOCUMENTS

| | | |
|---|---|---|
| CH | 475754 | 7/1969 |
| EP | 1 452 146 | 9/2004 |

* cited by examiner

*Primary Examiner* — Pedro Philogene
*Assistant Examiner* — David Comstock
(74) *Attorney, Agent, or Firm* — Wayne C. Jaeschke, Jr.

(57) ABSTRACT

A bone fixation system includes a bone fixation device, including a first element having a first channel extending therethrough and a second element including a proximal portion sized and shaped to be received within the first channel such that the longitudinal axes of the first and second elements are substantially coaxial and a distal portion including a bone engaging structure, a proximal end of the second element slidably locked within the first channel such that the first and second elements are longitudinally movable relative to one another between a permitted range of motion. The system also includes a driving tool, including an outer sleeve and an inner sleeve slidably received therethrough, a distal end of the outer sleeve configured to engage the proximal end of the first element to prevent relative rotation therebetween, a distal end of the inner sleeve configured to engage the proximal end of the second element.

22 Claims, 23 Drawing Sheets

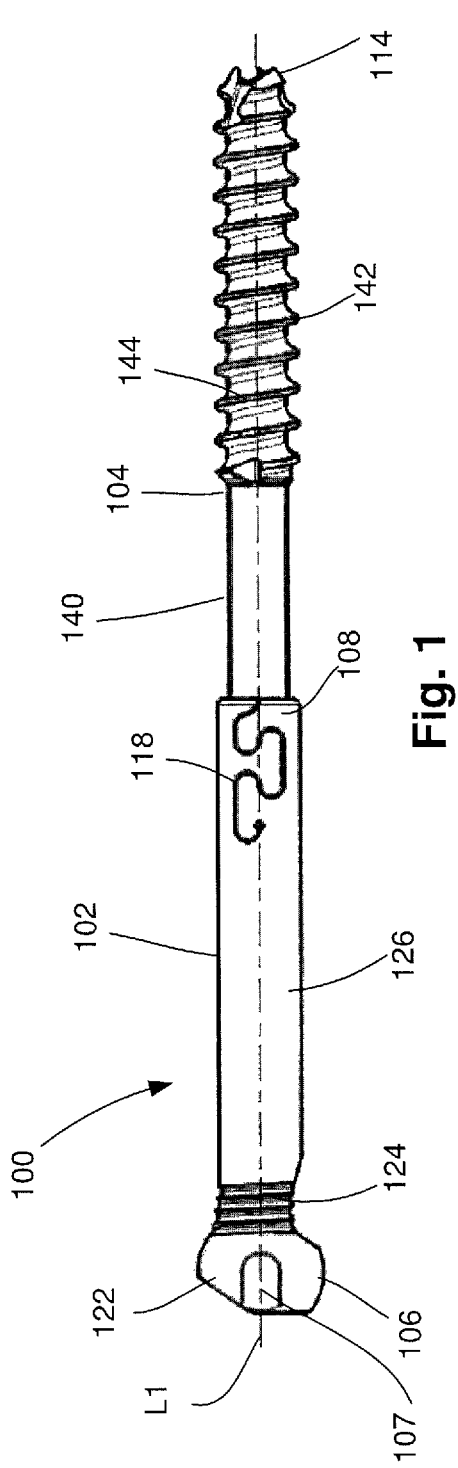

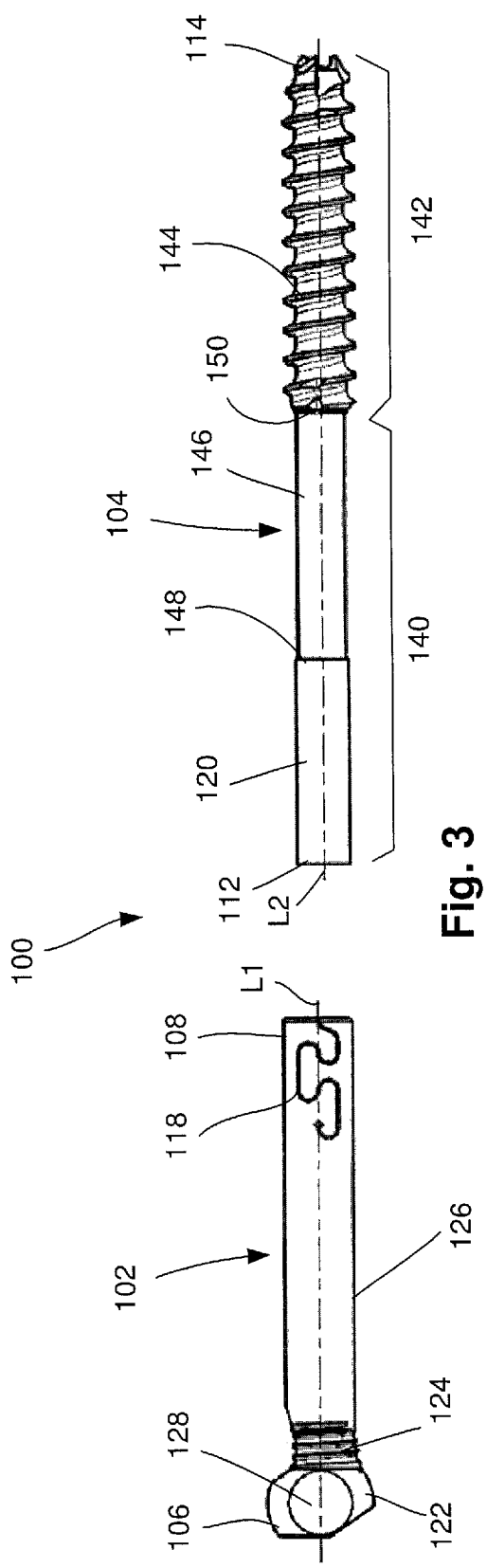
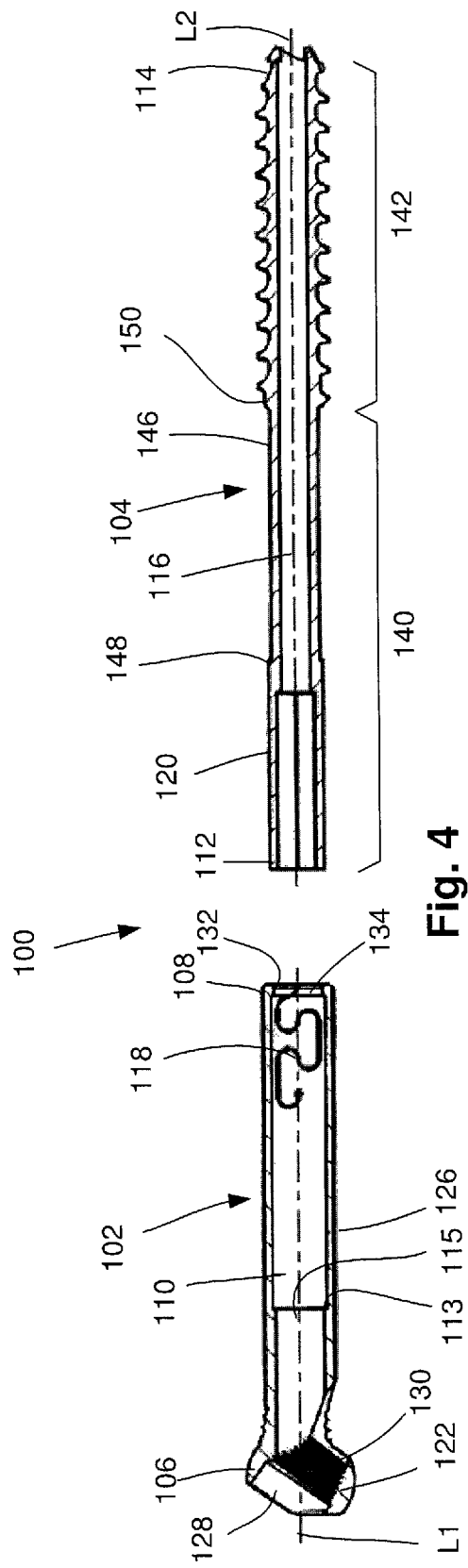
Fig. 3
Fig. 4

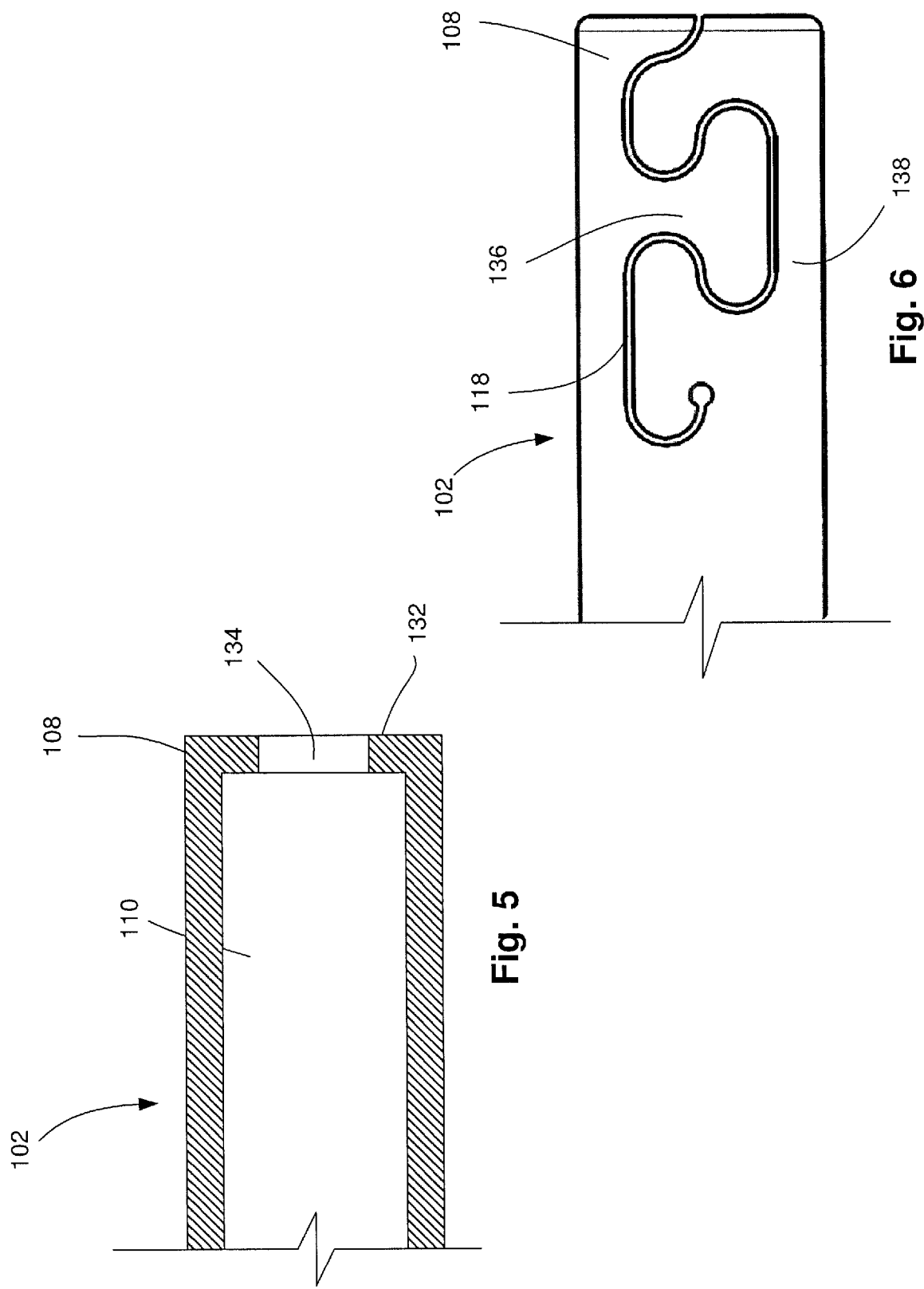

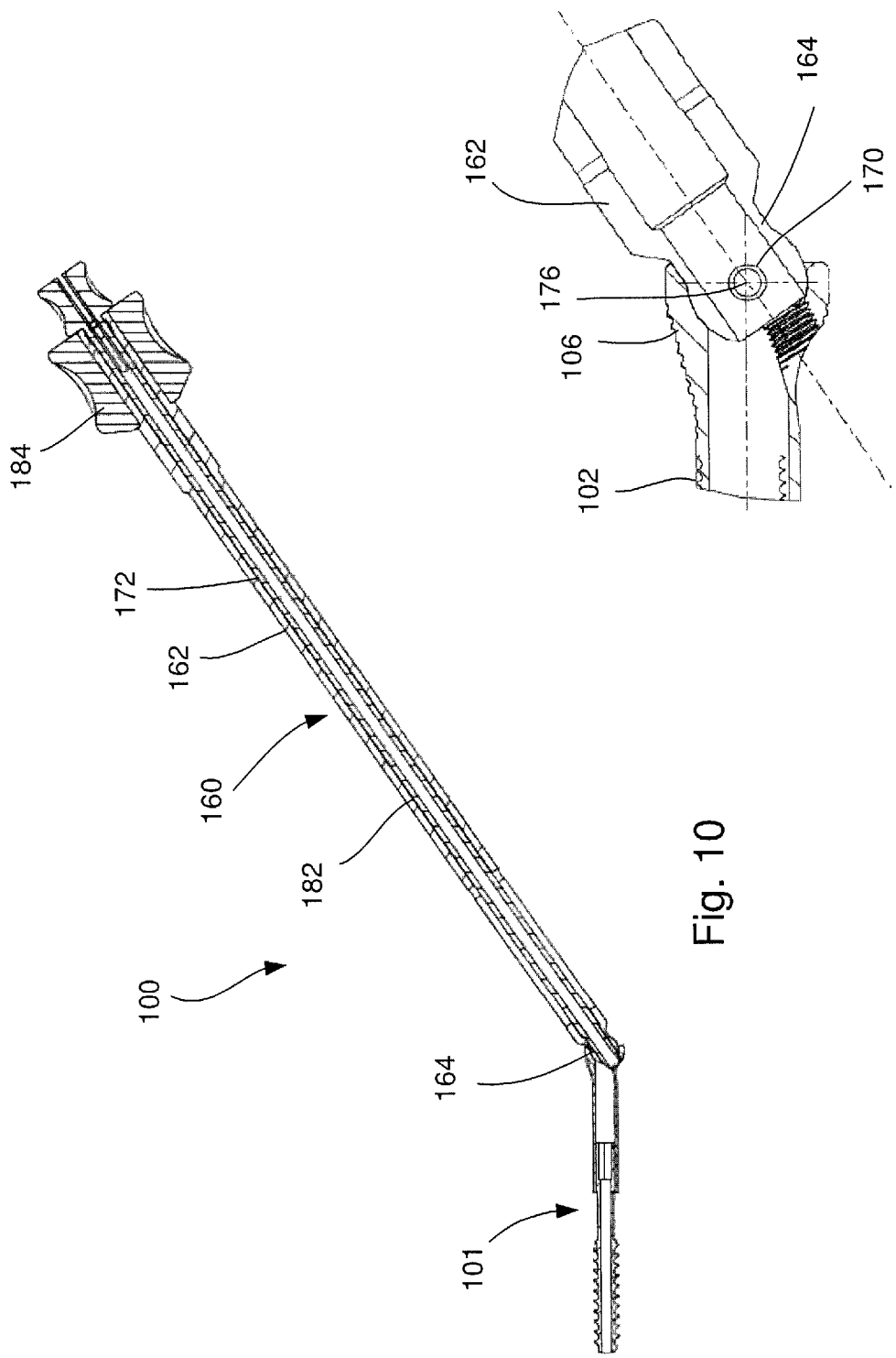

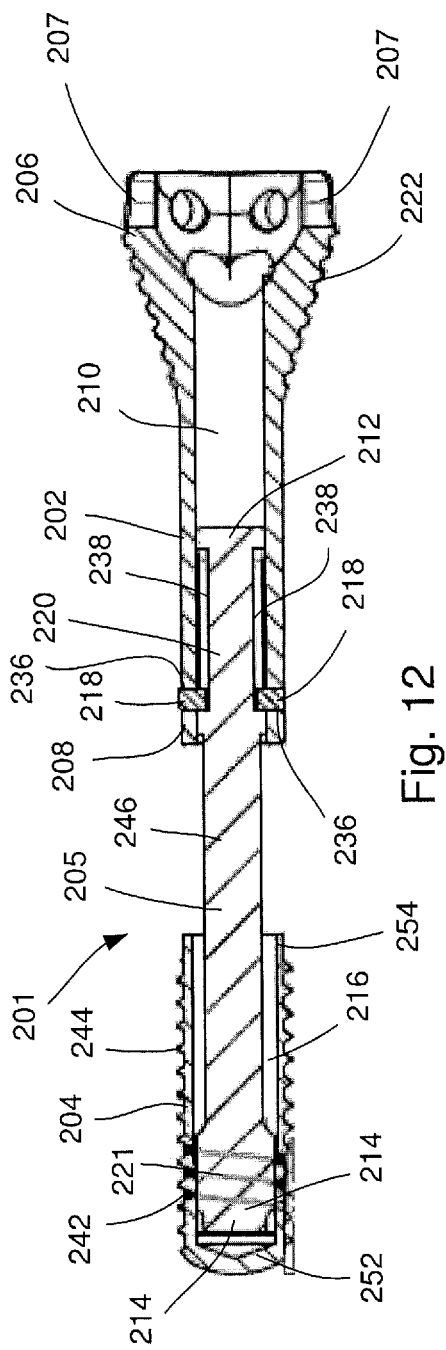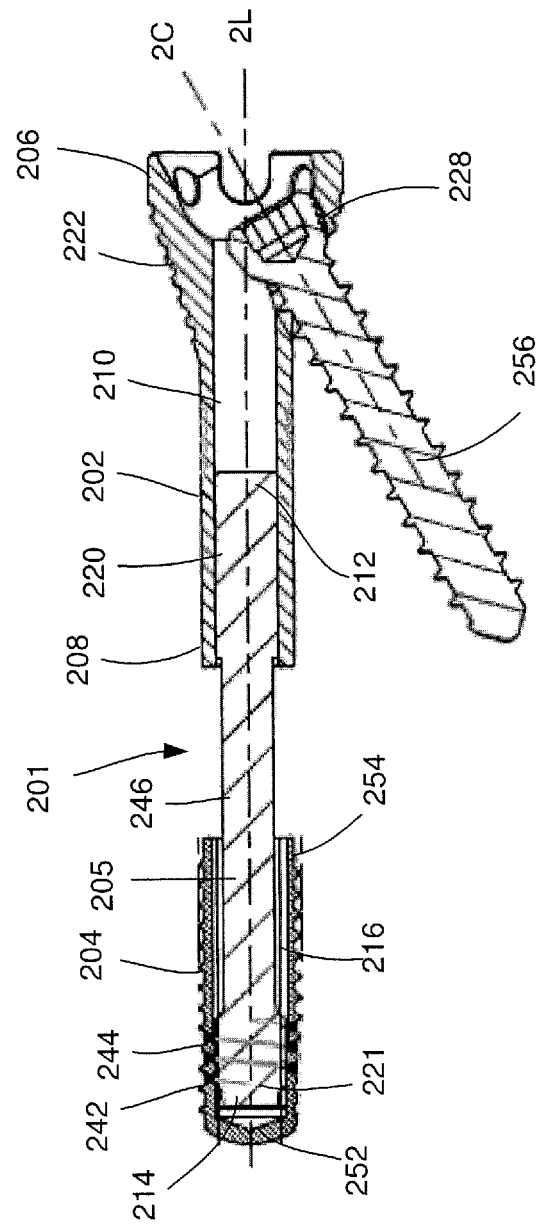
Fig. 12
Fig. 13

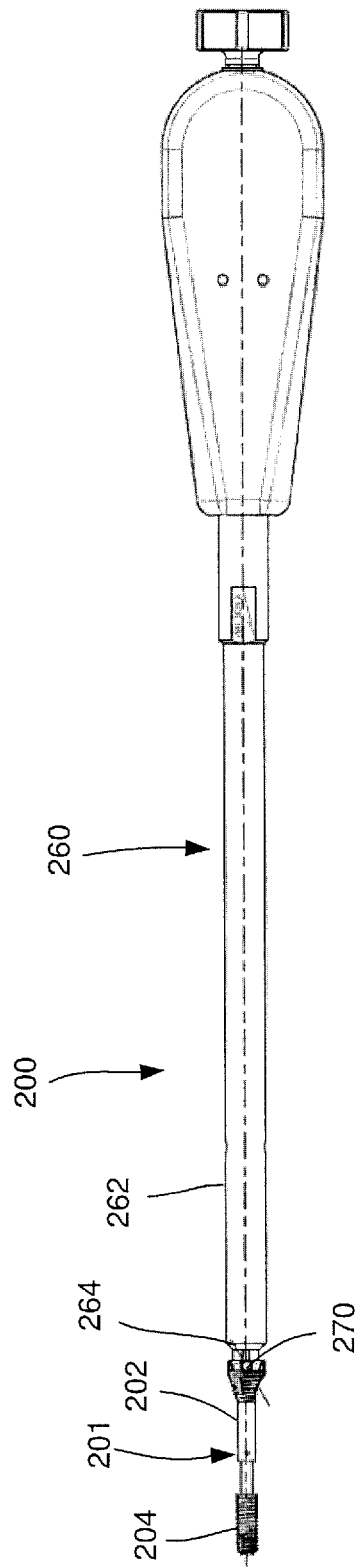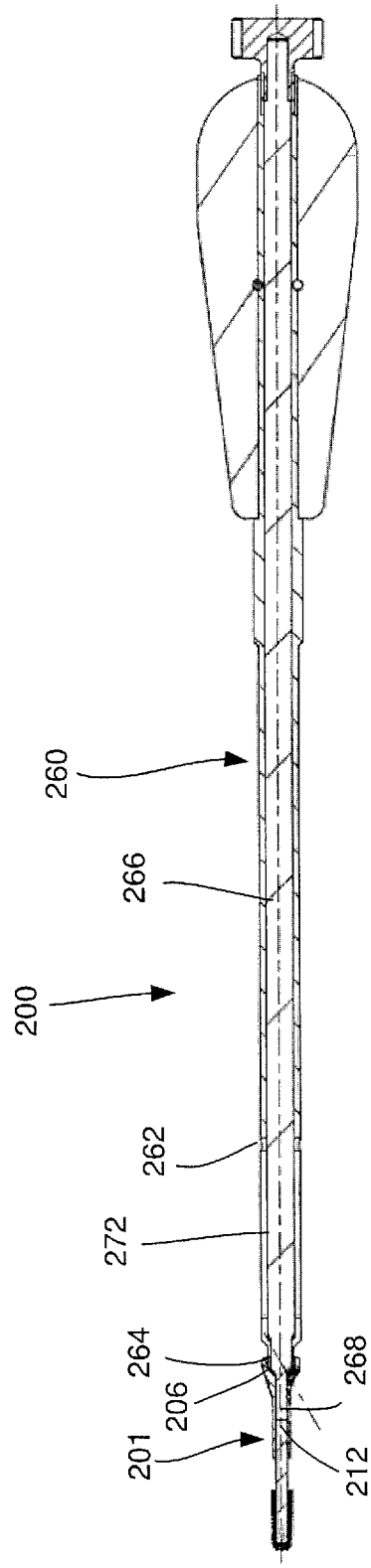

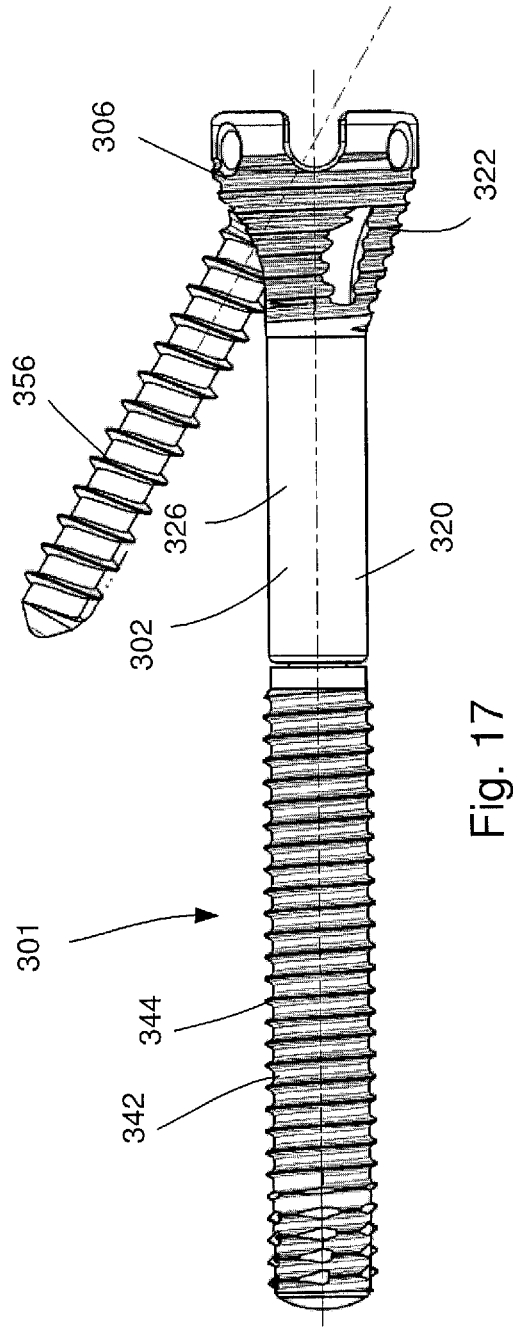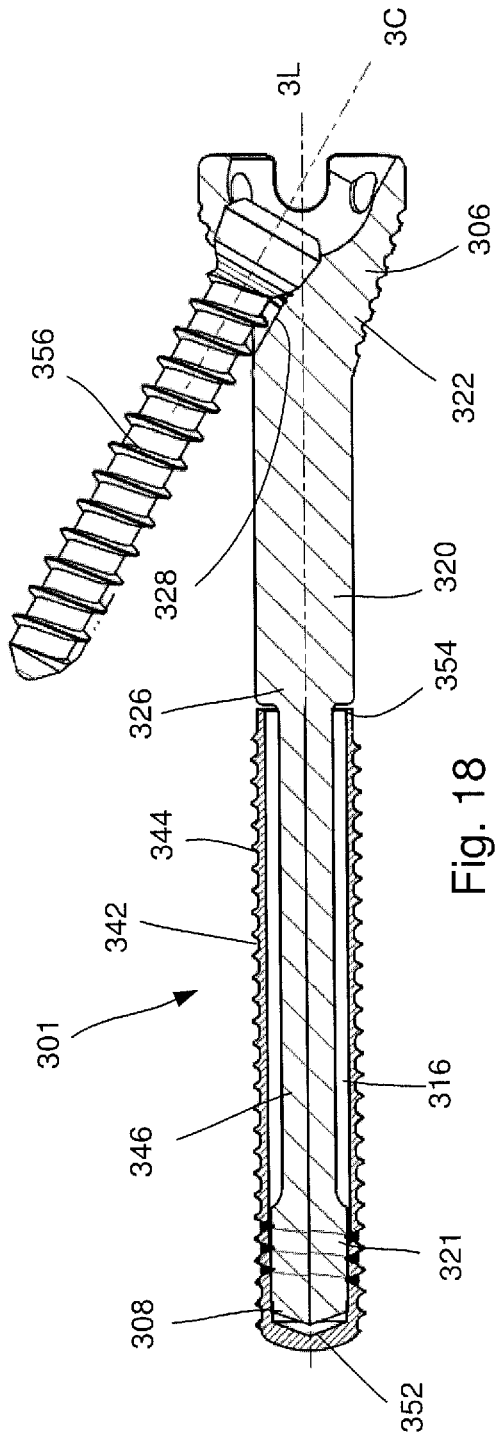

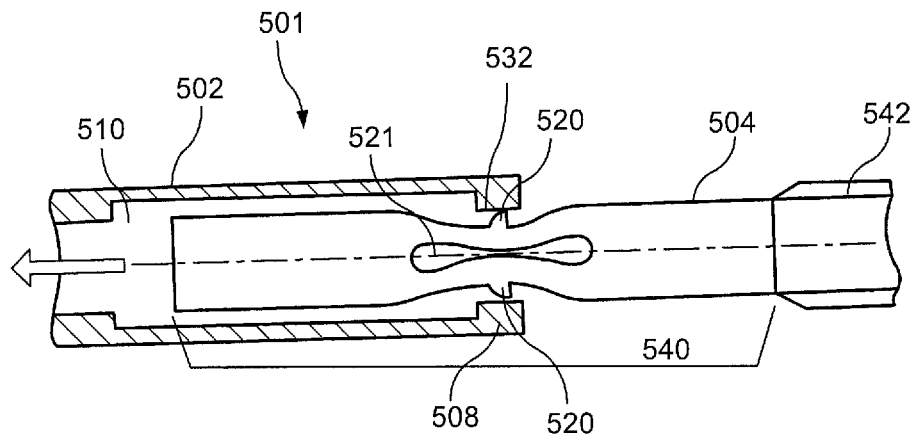
F I G. 23
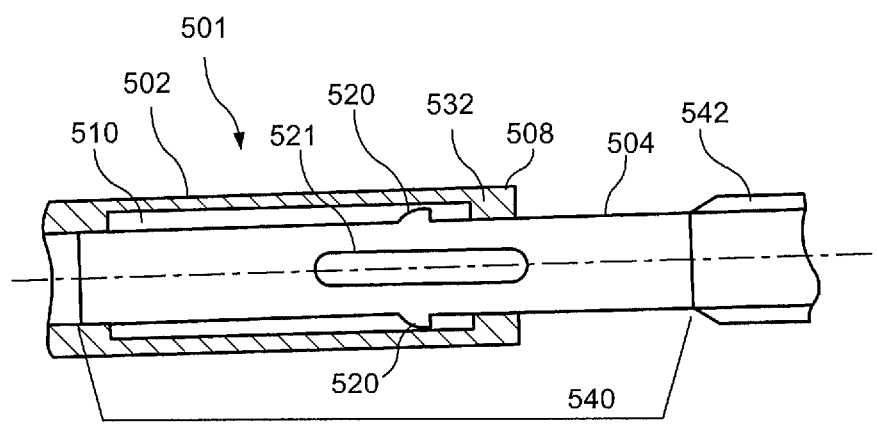
F I G. 24

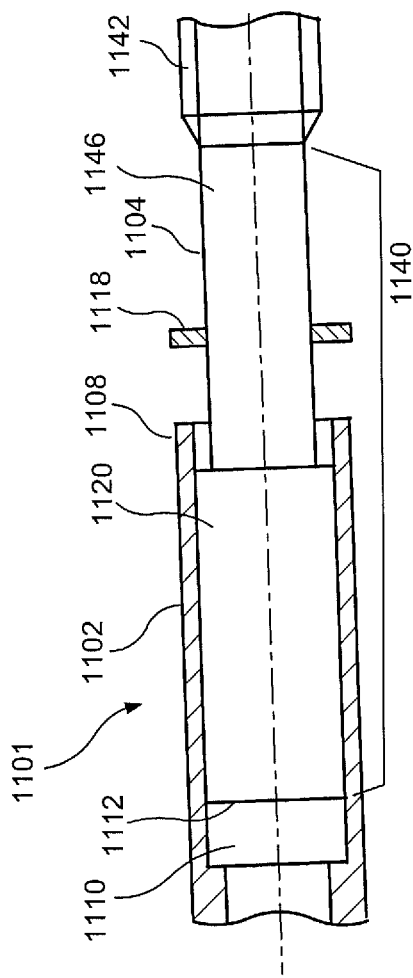
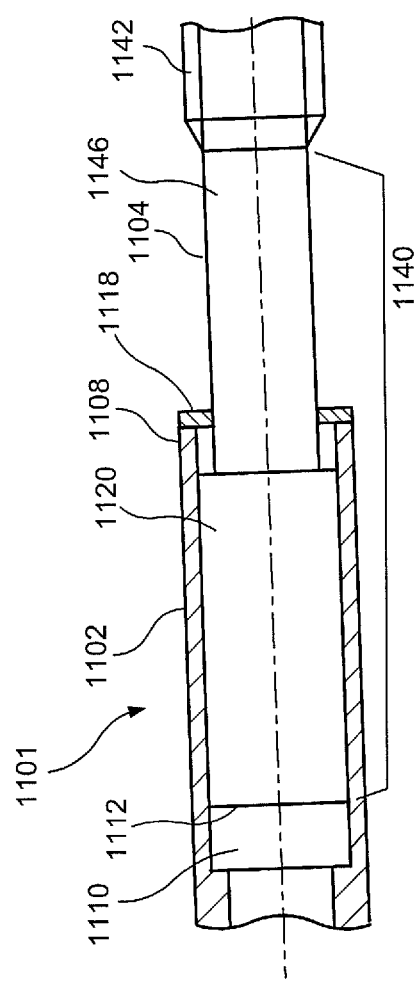
FIG. 37
FIG. 38

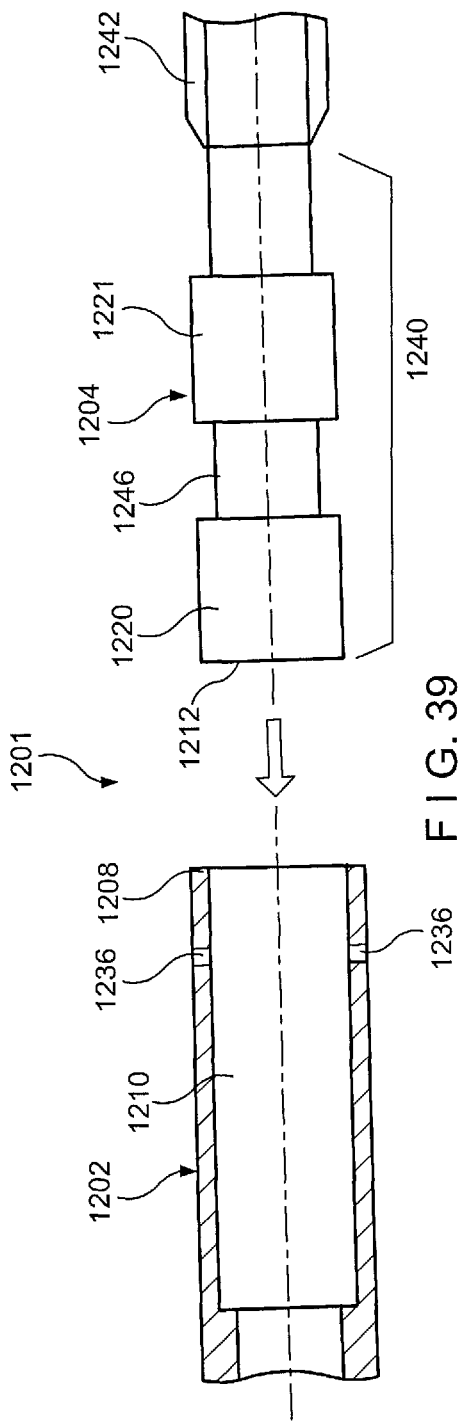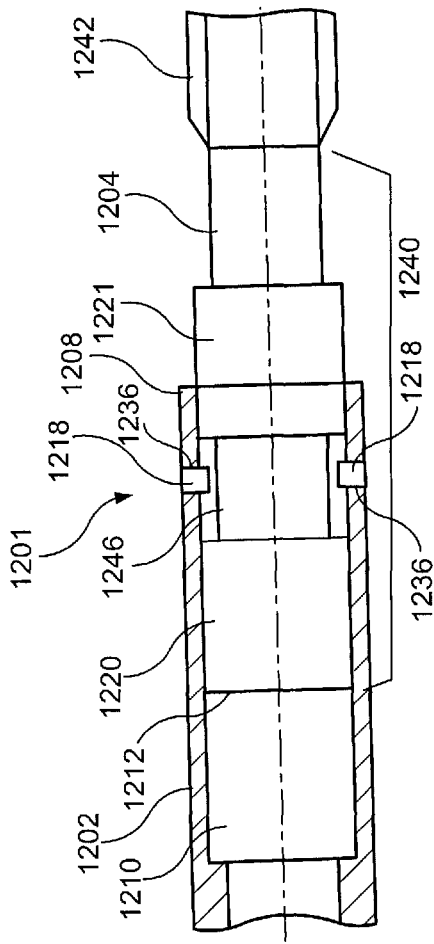

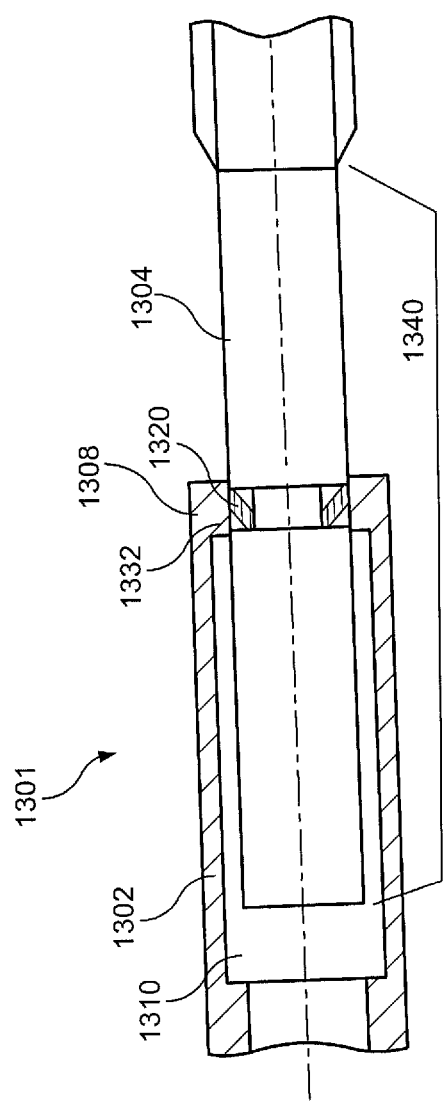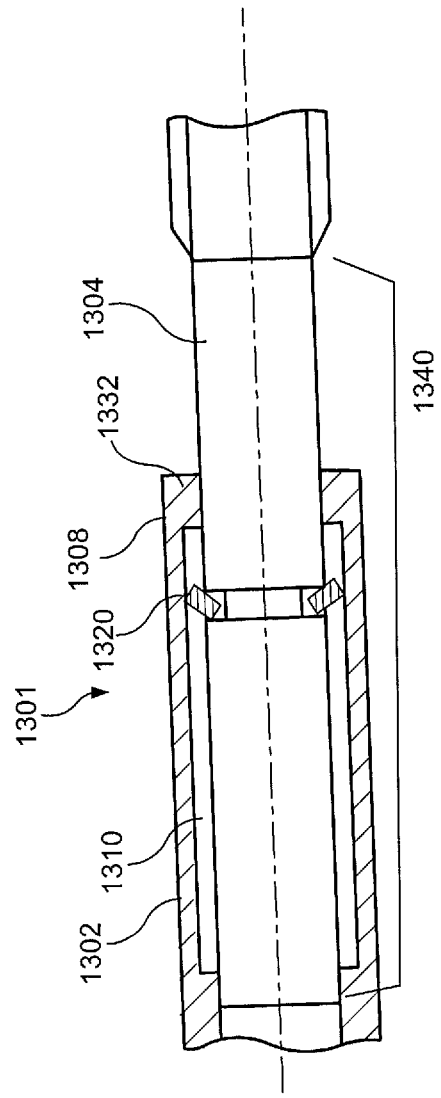

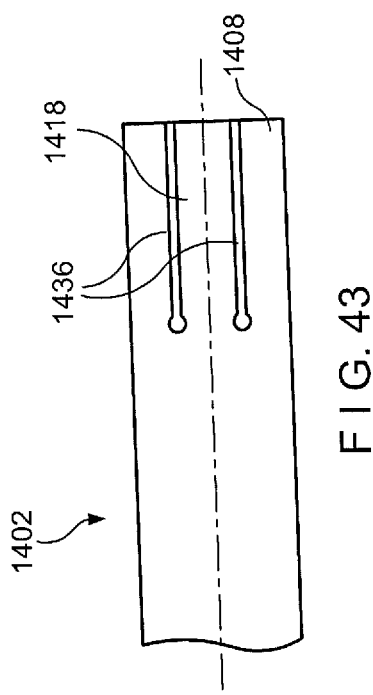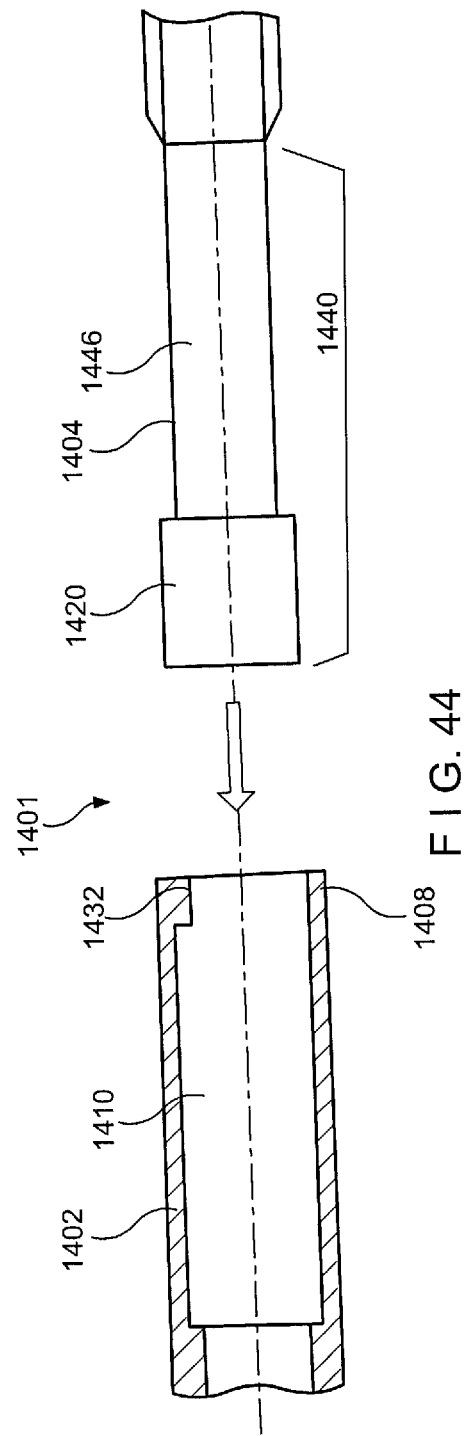

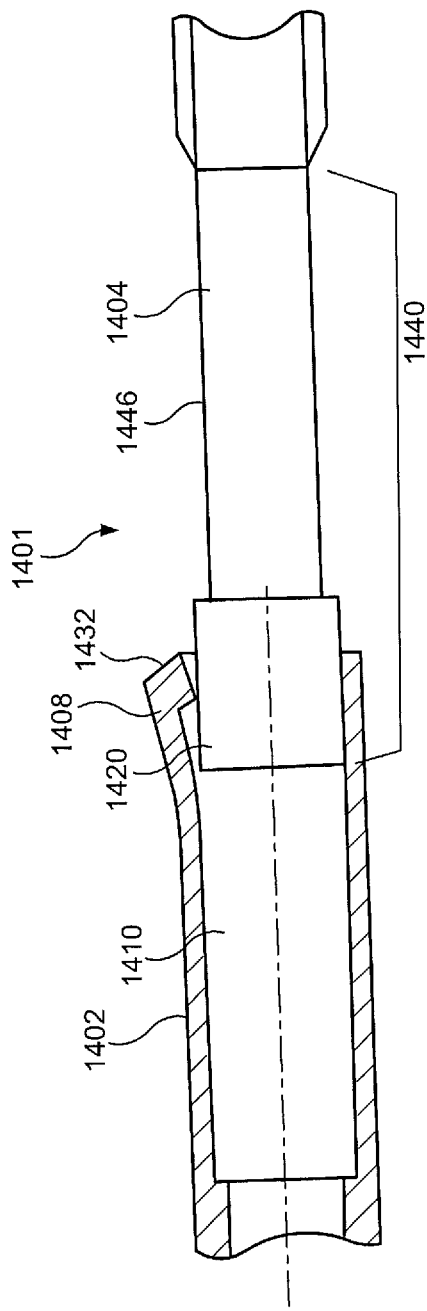
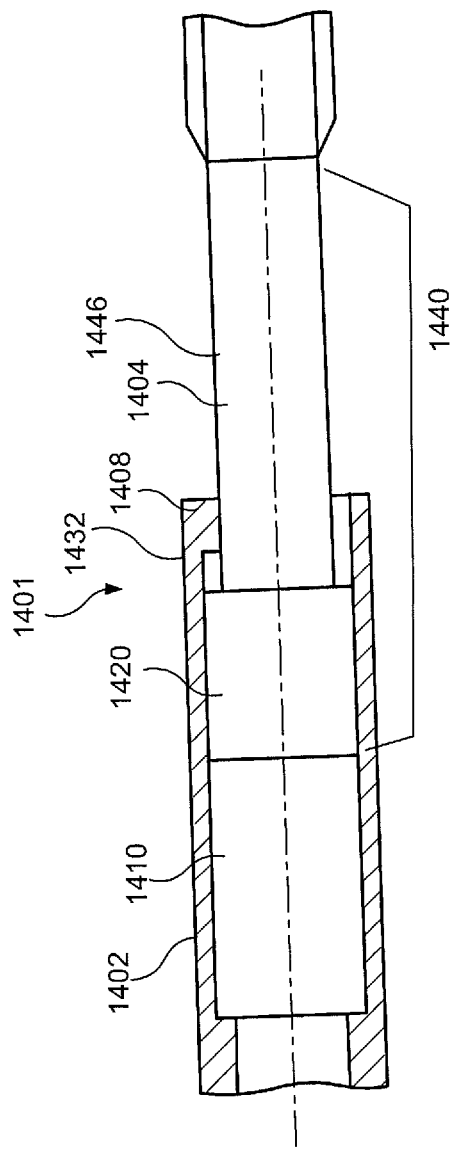
FIG. 45
FIG. 46

US 8,956,356 B2

TELESCOPING SCREW FOR FEMORAL NECK FRACTURES

PRIORITY CLAIM

The present invention claims priority to U.S. Provisional Application Ser. No. 61/487,140 filed on May 17, 2011 and entitled "Telescoping Screw for Femoral Neck Fractures," the entire disclosure of which is incorporated herein by reference.

FIELD OF THE INVENTION

The present invention relates to devices for treating a bone and, in particular, devices for treating bone fractures. An exemplary embodiment of the present invention describes a bone fixation device including first and second elements configured to telescope with respect to one another within a predetermined range of motion.

BACKGROUND

Telescoping screws have been used to fix various types of fractures and, in particular, have been employed to fix femoral neck fractures. Telescoping screws are particularly useful for fixing femoral neck fractures since the telescoping feature permits migration of the implanted screw while preventing the screw tip from penetrating the hip joint which is a significant risk for osteoporotic patients. Telescoping screws include stops configured to confine telescoping within a predetermined range. These stops, however, require a three piece assembly or a welding of different parts which may complicate these procedures.

SUMMARY OF THE INVENTION

The present invention is directed to a system for treating a bone, which includes a bone fixation device. The bone fixation device includes a first element extending along a first longitudinal axis from a proximal end to a distal end, the first element including a first channel extending therethrough along the first longitudinal axis and a second element extending along a second longitudinal axis from a proximal end to a distal end, the second element including a proximal portion sized and shaped to be received within the first channel such that the first and second longitudinal axes are substantially coaxial and a distal portion including a bone engaging structure, a proximal end of the second element slidably locked within the first channel such that the first and second elements are longitudinally movable relative to one another between a permitted range of motion. The bone fixation system further comprises a driving tool, including an outer sleeve extending longitudinally from a proximal end to a distal end and including a lumen extending therethrough, the distal end of the outer sleeve configured to engage the proximal end of the first element to prevent relative rotation therebetween and an inner sleeve slidable through the lumen of the outer sleeve and extending longitudinally from a proximal end to a distal end, the distal end of the inner sleeve configured to engage the proximal end of the second element.

BRIEF DESCRIPTION OF THE FIGURES

FIG. 1 shows a side view of a device according to an exemplary embodiment of the present invention;

FIG. 2 shows a cross-sectional side view of the device of FIG. 1 according to an exemplary embodiment of the present application;

FIG. 3 shows a side view of the device of FIG. 1, in a disassembled configuration;

FIG. 4 shows a cross-sectional side view of the device of FIG. 1, in the disassembled configuration;

FIG. 5 shows an enlarged cross-sectional side view of a distal end of a first element of the device of FIG. 1;

FIG. 6 shows an enlarged side view of the distal end of the first element of the device of FIG. 1;

FIG. 10 shows a cross-sectional side view of a portion of the driving tool of FIG. 7 pivoted with respect to the device of FIG. 1;

FIG. 11 shows an enlarged cross-sectional side view of a coupling between the driving tool of FIG. 7 and the device of FIG. 1, in a pivoted configuration;

FIG. 12 shows a cross-sectional side view of a device according to a second exemplary embodiment of the present invention;

FIG. 13 shows another cross-sectional side view of the device of FIG. 12;

FIG. 14 shows a side view of a driving tool for use with the device of FIG. 12;

FIG. 15 shows a cross-sectional side view of the driving tool of FIG. 12;

FIG. 17 shows a side view of a device according to a third exemplary embodiment of the present invention;

FIG. 18 shows a cross-sectional side view of the device of FIG. 17;

FIG. 23 shows a cross-sectional side view of a portion of a device according to another exemplary embodiment of the present invention, in a process of being assembled;

FIG. 24 shows a cross-sectional side view of the device of FIG. 23, in an assembled configuration;

FIG. 37 shows a cross-sectional side view of a portion of a device according to another exemplary embodiment of the present invention;

FIG. 38 shows a cross-sectional side view of the device of FIG. 37, in an assembled configuration;

FIG. 39 shows a cross-sectional side view of a portion of a device according to yet another exemplary embodiment of the present invention, prior to assembly;

FIG. 40 shows a cross-sectional side view of the device of FIG. 39, in an assembled configuration;

FIG. 41 shows a cross-sectional side view of a portion of a device according to another exemplary embodiment of the present invention, in a process of being assembled;

FIG. 42 shows a cross-sectional side view of the device of FIG. 41, in an assembled configuration;

FIG. 43 shows a side view of a portion of a first element of a device according to yet another exemplary embodiment of the present invention;

FIG. 44 shows a cross-sectional side view of a portion of a device of FIG. 43, prior to assembly;

FIG. 45 shows a cross-sectional side view of the device of FIG. 43, in a process of being assembled; and FIG. 46 shows a cross-sectional side view of he device of FIG. 43, in an assembled configuration.

DETAILED DESCRIPTION

Figure 7:
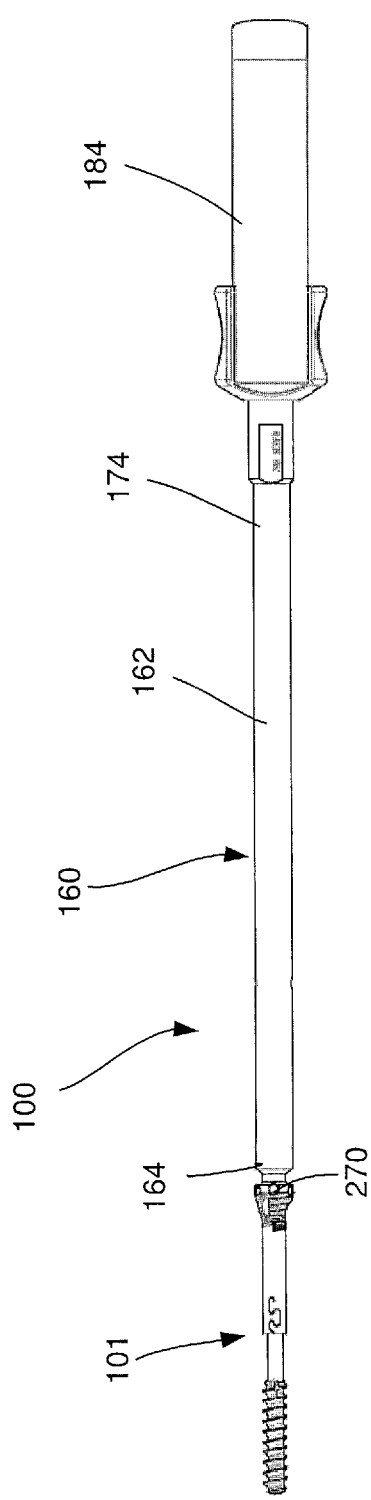
FIG. 7 shows a side view of a driving tool for use with the device of FIG. 1.
Figure 8:
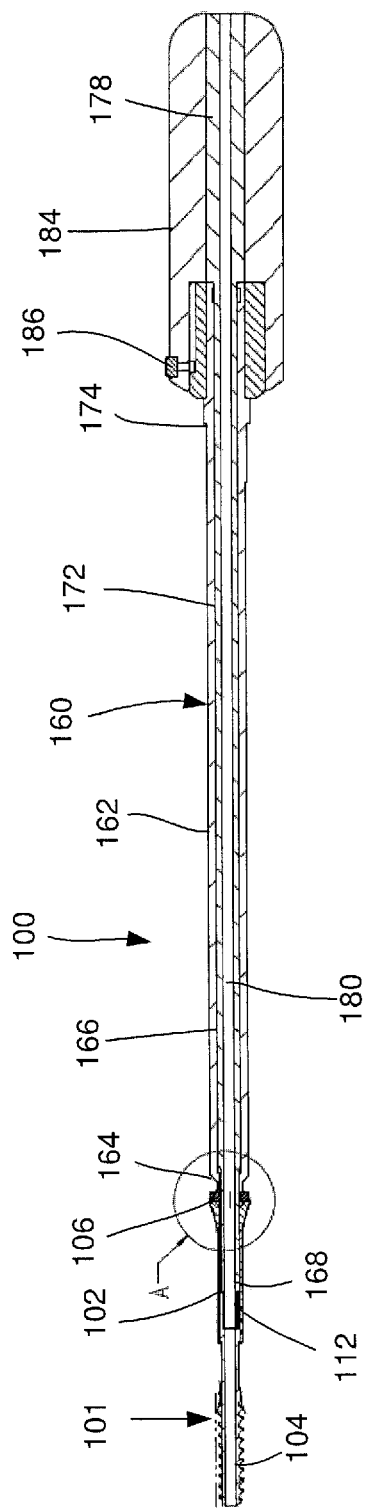
FIG. 8 shows a cross-sectional side view of the device of FIG. 7.
Figure 9:
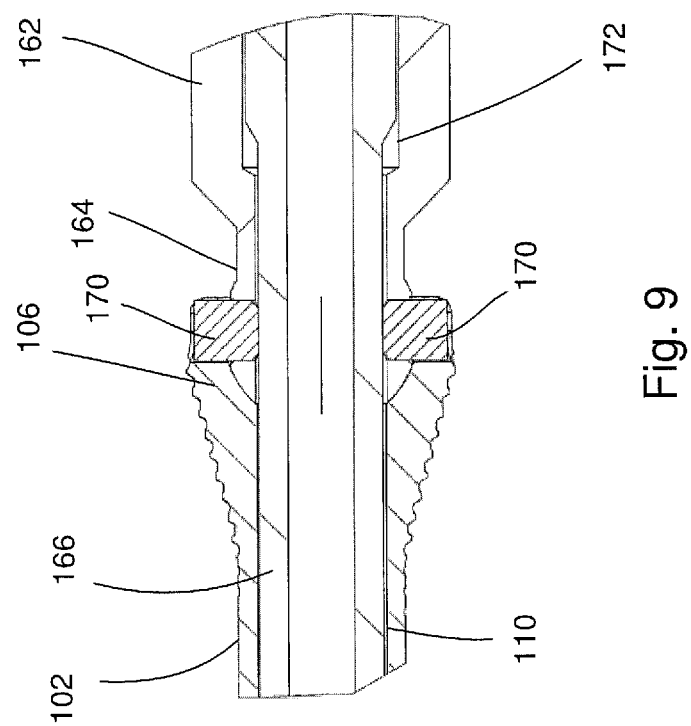
FIG. 9 shows an enlarged cross-sectional side view of a coupling between the device of FIG. 1 and the driving tool of FIG. 7.

The present invention may be further understood with reference to the following description and the appended drawings, wherein like elements are referred to with the same reference numerals. The present invention relates to devices for treating a bone and, in particular, devices for treating bone fractures. An exemplary embodiment of the present invention describes a bone fixation device including first and second elements configured to telescope with respect to one another within a predetermined range of motion. It should be noted that the terms "proximal" and "distal" as used herein, are intended to refer to a direction toward (proximal) and away from (distal) a user of the device.

A system 100 according to an exemplary embodiment of the present invention comprises a bone fixation device 101, as shown in FIGS. 1-6, including a first element 102 and a second element 104 received within the first element 102 such that the first and second elements 102, 104 telescope longitudinally (i.e., move relative to one another along longitudinal axis L1). The system 100 further comprises a driving tool 160, as shown in FIGS. 7-11, for driving the device 101 into the bone. The driving tool 160, as will be described in further detail below, includes an outer sleeve 162 having a distal end 164 configured to engage a proximal end 106 of the first element 102 and an inner sleeve 166 having a distal end 168 configured to engage a proximal end 112 of the second element 104 such that rotation of the driving tool 160 rotates the device 101 into the bone.

As shown in FIGS. 1-6, the first element 102 includes a first channel 110 extending therethrough and a slot 118 extending proximally from a distal end 108 thereof along a portion of a length thereof. As will be described below in more detail, the slot 118 is shaped to permit the distal end 108 of the first element 102 to expand by an amount required so that an enlarged proximal portion 120 of the second element 104 may be received within the first channel 110. Once the entire enlarged portion 120 has been received within the first channel 110 and an inner shoulder 132 formed at the distal end of the first channel 110 passes distally beyond a distal end 148 of the enlarged portion 120, the distal end 108 contracts under its natural bias so that the shoulder 132 locks the second element 104 within the channel 110, preventing the device 101 from becoming inadvertently disassembled. At this point, the second element 104 may slide within the channel 110 distally until the distal end 148 of the enlarged portion 120 contacts the shoulder 132 and proximally until a proximal end 112 of the enlarged portion 120 contacts a second inner shoulder 113 formed at the proximal end of the first channel 110 as will be described in more detail below.

In another embodiment, the second element 104 may slide within the channel 110 distally until the distal end 148 of the enlarged portion 120 contacts the shoulder 132 and proximally until a proximal end 150 of the bone engaging structure 144 contacts the distal end 108. It will be understood by those of skill in the art that other means for controlling the distal to proximal movement of the second element 104 relative to the first element 102 are also possible.

The first element 102 extends along a first longitudinal axis L1 from a proximal end 106 to a distal end 108 and includes the first channel 110 extending therethrough along the first longitudinal axis L1. The first element 102 includes a head 122 at the proximal end 106 and a shaft 126 extending distally therefrom. Threading 124 extends between the head 122 and the shaft 126 and/or along a portion of the head 122. The head 122 includes an opening 128 extending therethrough along a central axis angled with respect to the first longitudinal axis L1 at an acute angle. As would be understood by those skilled in the art, the opening 128 is sized and shaped to receive a bone fixation element (e.g., bone screw) and may include threading 130 along a portion of an inner surface thereof for engaging threading on a bone fixation element inserted therein. The threaded portion 124 extends along an exterior of the first element 102 between the head 122 and the shaft 126 and is configured, for example, to engage a bone plate and/or a portion of a bone through which the bone fixation device 101 is inserted. The proximal end 106 may also be configured to engage the outer sleeve 162 of the driving tool 160. For example, the proximal end 106 may include a pair of recesses 107 extending therein along opposing sides thereof. The recesses 107 may be sized and shaped to receive corresponding protrusions 170 along the distal end 164 of the outer sleeve 162 of the driving tool 160 such that the outer sleeve 162 may be pivoted with respect to the longitudinal axis L1, as will be described in further detail below.

As described above and as shown in FIG. 5, the distal end 108 includes a shoulder 132 extending radially inward such that a diameter of an opening 134 of the first channel 110 at the distal end 108 is smaller than a diameter of a portion of the first channel 110 distal thereof and so that the diameter of the opening 134 is smaller than an outer diameter of the enlarged portion 120 of the second element 104. In an exemplary embodiment, a diameter of the opening 134 is approximately 0.2 mm smaller than a diameter of the portion of first channel 110 proximal thereto. The slot 118 extends along the shaft 126 proximally from the distal end 108 along a curved path so that portions of opposite sides of the slot 118 interlock to limit radial expansion of the distal end 108 to an amount no more than a desired maximum expansion. As shown in FIG. 6, the slot 118 extends through the shaft 126 along a curve defining first and second interlocking parts 136, 138, respectively, on opposite sides of the slot 118. The first and second parts 136, 138, respectively, are shaped to mechanically engage one another when the distal end 108 has expanded to the point at which the parts mechanically engage (i.e., the width of at least a portion of the slot 118 is reduced to zero). The distal end 108 is elastically movable between a non-expanded configuration and an expanded configuration. In particular, the first and second interlocking parts 136, 138 are capable of moving apart from one another to expand the distal end 108 by a distance substantially corresponding to a width of the slot 118 while preventing the first and second interlocking parts 136, 138 from disengaging one another. So that the distal end 108 of the first element 102 may expand to receive the second element 104, at least the distal end 108 should be formed of a material having sufficient elasticity to expand to the desired degree and return to the non-expanded shape once the entire enlarged portion 120 has been moved proximally beyond the shoulder 132. It will be understood by those of skill in the art, however, that an entire length of the shaft 126 or other portions thereof may also be formed of the same material as the distal end 108. It will be understood by those of skill in the art that the shaft 126 may be made from any of a number of different possible materials. For example, the shaft 126 may be formed of cobalt chromium, stainless steel, titanium and/or alloys thereof.

The second element 104 extends along a second longitudinal axis L2 from a proximal end 112 to a distal end 114 and includes a second channel 116 extending therethrough along the second longitudinal axis L2. The second element 104 includes a proximal portion 140 slidable within the first channel 110 of the first element 102 and a distal portion 142 including a bone engaging structure 144 extending along a length thereof. As would be understood by those skilled in the art, the bone engaging structure 144 may include, for example, threading. It will be understood by those of skill in the art, however, that the bone engaging structure 144 may be any of a variety of structures capable of engaging bone such as, for example, helical blade, protrusions, etc.

The proximal portion 140 of the second element 104 further includes the enlarged portion 120 at a proximal end thereof. The enlarged portion 120 extends radially outward from the proximal portion 140 and is sized and shaped to be slidably accommodated within the first channel 110. A remaining length 146 of the proximal portion 140 is sized and shaped to be slidably received within the opening 134 of the first channel 110. Thus, a distal-most position of the second element 104 relative to the first element 102 is defined by contact between a distal end 148 of the enlarged portion 120 and the shoulder 132 forming the opening 134, which prevents the enlarged portion 120 from moving distally past the shoulder 132. In one exemplary embodiment, the second element 104 is rotatable relative to the first element 102 so that a driving tool may be inserted through the first element 102 to engage the proximal end 112 of the second element 104. The driving tool may then be rotated to screw the second element 104 into a bone. For example, the proximal end 112 may include a hexagonal recess sized and shaped to receive a hexagonal portion of a driving tool. It will be understood by those of skill in the art, however, that a recess extending through the proximal end 112 may be any of a variety of shapes and sizes so long as the proximal end 112 is configured to receive a driving tool capable of applying a torsional force thereto. In another embodiment, the first channel 110 and the enlarged portion 120 may be keyed to one another via, for example, corresponding planar surfaces along lengths thereof, such that the first and second elements 102, 104 are prevented from rotating relative to one another.

The enlarged portion 120 has a lateral cross-section (e.g., diameter) larger than an opening 115 of the second shoulder 113 such that the second element 104 is prevented from moving any farther proximally relative to the first element 102 when the proximal end 112 of the enlarged portion 120 contacts the shoulder 113. Thus, a permitted range of motion of the first and second elements 102, 104 relative to one another is defined by a contact between the distal end 148 of the enlarged portion 120 and the shoulder 132 and a contact between the proximal end 112 of the enlarged portion 120 and the additional shoulder 113, when the first and second elements 102, 104 are connected to one another.

Other ways of restricting the movement of the second element 104 relative to the first element 102 are also possible. In one example, the distal portion 142 has a lateral cross-section (e.g., diameter) larger than the opening 134 such that the second element 104 is prevented from moving any farther proximally relative to the first element 102 when a proximal end 150 of the distal portion 142 contacts the shoulder 134. Thus, in this example, a permitted range of motion is defined by a distance between the distal end 148 of the enlarged portion 120 and the proximal end 150 of the distal portion 142.

The first and second elements 102, 104 are assembled by inserting the enlarged portion 120 of the second element 104 into the first channel 110 of the first element 102. The enlarged portion 120 is inserted into the first channel 110 causing the distal end 108 of the shaft 126 to expand. The distal end 108 expands as the first and second interlocking parts 136, 138 defined by the slot 118 move away from one another to permit the enlarged portion to be received therein. Once the enlarged portion 120 has been inserted into the first channel 110 proximally past the shoulder 132, the distal end 108 reverts back to the non-expanded configuration under its natural bias with the shoulder 132 surrounding the reduced diameter length 146 of the proximal portion 140 of the second element 104. While the slot 118 permits the distal end 108 to expand to receive the enlarged portion 120 therein, the first and second interlocking parts 136, 138 prevent the distal end 108 from opening beyond a desired amount (i.e., an amount corresponding to a space required to permit the enlarged portion 120 to be received therein). Thus, lateral forces applied to the distal portion 142 of the second element 104 will not cause the distal end 108 to open beyond the desired amount. The first and second elements 102, 104 in this embodiment are substantially coaxial when assembled (i.e., the first and second longitudinal axes are substantially coaxial). In a preferred embodiment, the first and second elements 102, 104 are assembled during manufacturing of the device 101. It will be understood by those of skill in the art, however, that the device 101 may also be assembled after manufacturing, prior to the usage of the device 101.

Once the device 101 has been assembled as described above, the first and second elements 102, 104 are longitudinally slidable relative to one another. The second element 104 is permitted to slide relative to the first element 102 between a distal-most position relative to the first element 102 in which the distal end 148 of the enlarged portion 120 abuts the shoulder 132 and a proximal-most position relative to the first element 102 in which the proximal end 112 of the enlarged portion 120 abuts the shoulder 113. The device 101 is particularly suited for fixing femoral neck fractures as the extent of telescoping permitted may be selected to prevent the distal end 114 of the distal portion 142 from penetrating into the joint. It will be understood by those of skill in the art, however, that the device 101 may be used in any of a variety of bones in which the sliding movement of the first and second elements 102, 104 would be desired.

The bone fixation device 100 may be inserted into the bone using, for example, the driving tool 160, as shown in FIGS. 7-11. The driving tool 160 comprises an outer sleeve 162 and an inner sleeve 166 receivable within a lumen 172 of the outer sleeve 162. The outer sleeve 162 extends longitudinally from a proximal end 174 to the distal end 164, which is configured to be releasably coupled to the proximal end 106 of the first element 102 of the bone fixation device 101. The distal end 164 may be substantially spherical and may, for example, include a pair of protrusions 170 extending radially outward from opposing sides thereof. The protrusions 170 are sized and shaped to be received within corresponding recesses 107 extending through the proximal end 106 of the bone fixation device 101. The protrusions 170 may, for example, be snapped into the recesses 107. Rotation of the outer sleeve 162 correspondingly rotates the first element 102. In addition, as shown in FIGS. 10 and 11, the outer sleeve 162 may be pivoted relative to the bone fixation element 101 about a pivot axis 176 such that a longitudinal axis of the outer sleeve 162 may be angled with respect to the longitudinal axis L1 such that the lumen 172 is aligned with the opening 128 of the first element 102. The lumen 172 may be sized and shaped to accommodate a drill guide 182 therein such that a hole may be drilled through the bone along a path corresponding to the central axis of the opening 128.

The inner sleeve 166 extends longitudinally from a proximal end 178 to the distal end 168 and includes a lumen 180 extending therethrough. The lumen 180 may be sized and shaped to accommodate a guide wire therein for guiding the bone fixation device 101 along a desired path into the fractured bone. The distal end 166 is configured to engage the proximal end 112 of the second element 104. For example, the distal end 166 may be hexagonally shaped to be received within a corresponding hexagonal recess within the proximal end 112. Thus, rotation of the inner sleeve 166 correspondingly rotates the second element 104 such that the bone fixation device 101 may be driven into the bone. It will be understood by those of skill in the art, however, that the distal end 166 of the inner sleeve 166 and the proximal end 112 of the second element 104 may be any of a variety of corresponding shapes and sizes so long as engagement between the inner sleeve 166 and the proximal end 112 permits a torsional force to be transmitted therebetween.

The driving tool 160 may further comprise a handle 184 coupled to the proximal end 178 of the inner sleeve 166 and couplable to the proximal end 174 of the outer sleeve 162. The handle 184 may be coupled to the outer sleeve 162 via, for example, a pin 186 such that the outer and inner sleeve 162, 166 are prevented from rotating relative to one another. In this way, when the pin 186 is not engaged with the outer sleeve 162, the inner and outer sleeve can be rotated independently of one another to selectively transmit a torsional force to both the first and second elements 102, 104 of the bone fixation device 101. Alternatively, when the pin 186 is engaged with the outer sleeve 162, rotation of the handle 184 rotates both the outer and inner sleeves 162, 166 to transmit a torsional force to both the first and second elements 102, 104 of the bone fixation device 101. The driving tool 160 may also include markings along the handle 184 or other portion thereof (e.g., a proximal portion of the driving tool 160) indicating to a user which direction the outer sleeve 162 should be pivoted relative to the bone fixation device 101 for the lumen 172 to be aligned with the opening 128.

According to a surgical technique using the system 100, the bone fixation device 101 may be inserted into a bone using the driving tool 160. Once the first and second elements 102, 104 of the bone fixation device 101 have been assembled as described above, the driving tool 160 may be coupled to the proximal ends 106, 112 of the first and second elements 102, 104, respectively. Specifically, the user engages the distal end 164 of the outer sleeve 162 with the proximal end 106 of the first element 102 by, for example, snapping the protrusions 170 of the distal end 164 into the corresponding recesses 107 along the proximal end. The user engages the distal end 168 of the inner sleeve 166, which extends through the lumen 172 of the outer sleeve 162, with the proximal end 112 of the second element 104 by, for example, inserting the distal end 166 (e.g., a hexagonally shaped end) into a correspondingly sized and shaped recess in the proximal end 112. The coupled bone fixation device 101 and the driving tool 160 may then be slid over a guide wire along a desired path into the fractured bone. The driving tool 160 is then rotated via the handle 184 to drive the bone fixation device 101 into the bone. As described above, rotation of the handle 184 can rotate both the first and second elements 102, 104 of the bone fixation device 101 simultaneously or independently at the discretion of a user and depending on the engagement of disengagement of the pin 186 with the outer sleeve 162. The simultaneous rotation with the pin 186 in an engagement position is used, for example, when a user wants to limit telescoping or axial translation of the first and second elements 102, 104 relative to one another. The simultaneous rotation is useful during, for example, initially positioning and inserting of the bone fixation elements 101 into a bone. The independent rotation with the pin 186 in a disengaged position is useful in a number of scenarios. For example, rotating the inner sleeve 166 independently of the outer sleeve 162 when the bone fixation element 101 is positioned in the bone enables, for example, active compression. Specifically, the second element 104 is rotated by the inner sleeve 166 and the first element 102 is held stationary by the outer sleeve 162, which causes an active compression since the second element 104 can be advanced further into a bone to which it is connected and thereby draw that bone towards the first element 102. In another example, rotation of the outer sleeve 162 independently of the inner sleeve 166 allows, for example, the threading 124 to advance further into a part of the bone to which the first element 102 is connected without causing additional compression. In a further example, rotation of the outer sleeve 162 independently of the inner sleeve 166 allows the opening 128 to be orientated in a manner defining a desired axis of orientation for insertion of a second screw into the bone without causing unnecessary rotation of the second element 102. An example of the insertion of the second screw is illustrated in FIG. 12 and described in more detail below with reference to bone fixation element 201. Once the bone fixation device 101 has been driven into the bone, as desired, the inner sleeve 166 and the guide wire may be removed from the lumen 172 of the outer sleeve 162. The inner sleeve 166 may be removed by loosening the pin 186 such that the inner sleeve 166 may be pulled proximally therefrom.

The outer sleeve 162 is then pivoted about the pivot axis 176 such that the lumen 172 is aligned with the central axis of the opening 128 extending through the first element 102, as shown in FIG. 11. Once the outer sleeve 162 has been pivoted, as desired, the drill guide 182 is inserted into the lumen 172, as shown in FIG. 10, such that a hole may be drilled in the bone along the central axis of the opening 128. A bone fixation element such as a bone screw may then be inserted through the opening 128 and into the drilled hole until a threading along a head portion of the bone screw engages the threading 130 along the interior of the opening 128. Alternatively, the bone screw may be drilled into the bone directly through the lumen 172 of the outer sleeve 162. Once inserted, a shaft of the bone screw extends along the central axis of the opening 128, at an angle relative to the longitudinal axis L1 of the bone fixation device 101 to provide additional fixation thereof.

As shown in FIGS. 12-16, a system 200 according to another exemplary embodiment of the present invention is substantially similar to the system 100 described above, comprising a bone fixation device 201 and a driving tool 260. The bone fixation device 201, as shown in FIGS. 12-13, may be substantially similar to the bone fixation device 101, including a first element 202 and a second element 204 which telescope with respect to one another. Similarly, the first element 202 extends longitudinally from a proximal end 206 to a distal end 208 and includes a channel 210 extending longitudinally therethrough. The first element 202 also includes an opening 228 extending through a head portion 222 thereof along a central axis 2C angled with respect to a longitudinal axis 2L of the bone fixation device 201 such that a bone fixation element such as a bone screw 256 is insertable therein along the central axis 2C. The first element 202, however, does not include a slot, opposite sides of which interlock to permit expansion of the distal end 208 to receive an enlarged proximal portion 220 of the second element 204. Rather, the enlarged proximal portion 220 is received within channel 210 and held therein via a pin 218 received within a corresponding hole 236 extending through the first element 202 and a longitudinal groove 238 extending along the enlarged portion 220, as will be described in further detail below.

The second element 204 includes a shaft 205 and a bone engaging member 242 in which a distal end 214 of the shaft 205 is received. The bone engaging member 242 includes threading 244 extending along an exterior thereof and includes a channel 216 extending longitudinally therethrough from a closed distal end 252 to an open proximal end 254. The shaft 205 extends from a proximal end 212 to a distal end 214 and includes an enlarged proximal portion 220 and an enlarged distal portion 221 connected to one another via a mid portion 246 having a smaller circumference (e.g., diameter) than both the enlarged proximal and distal portions 220, 221. The enlarged distal portion 221 is sized and shaped to be received within the channel 216 of the bone engaging member and is fixed within a distal portion of the channel 216 such that a portion of the mid portion 246 extends through a proximal portion of the channel 216. The mid portion 246 has a smaller diameter than the enlarged distal portion 221 and the channel 216 such that bone engaging member 242 is permitted to deflect with respect to the shaft 205 to provide dynamization of the bone fracture. It will be understood by those of skill in the art that a range of deflection of the bone engaging member 242 is determined by the size of the channel 216 relative to the size of the mid portion 246.

The enlarged proximal portion 220 of the second element 204 is sized and shaped to be received within the channel 210 of the first element 202. As described above, however, the enlarged proximal portion 220 is held therein via a pin 218 extending through the corresponding hole 236 in the first element 202 and the longitudinal groove 238 extending along the enlarged proximal portion. A length of the groove 238 determines a range of sliding motion between the first and second elements 202, 204. Specifically, the second element 204 may be longitudinally slid relative to the first element 202 such that the pin 218 is slidable between proximal and distal ends of the groove 238. The pin 218 also prevents the first and second elements 202, 204 from being rotated relative to one another. Thus, a driving force applied to the first element 202 correspondingly rotates the second element 204. In one exemplary embodiment, the bone fixation device 201 may include two pins 218, two corresponding holes 236 and two longitudinal grooves 238 on opposing sides thereof. It will be understood by those of skill in the art, however, that the bone fixation device 201 may include any number of corresponding pins 218, holes 236 and grooves 238 so long as the pin 218 permits the first and second elements 202, 204 to be longitudinally movable relative to one another while preventing the first and second elements 202, 204 from rotating relative to one another.

Figure 16:
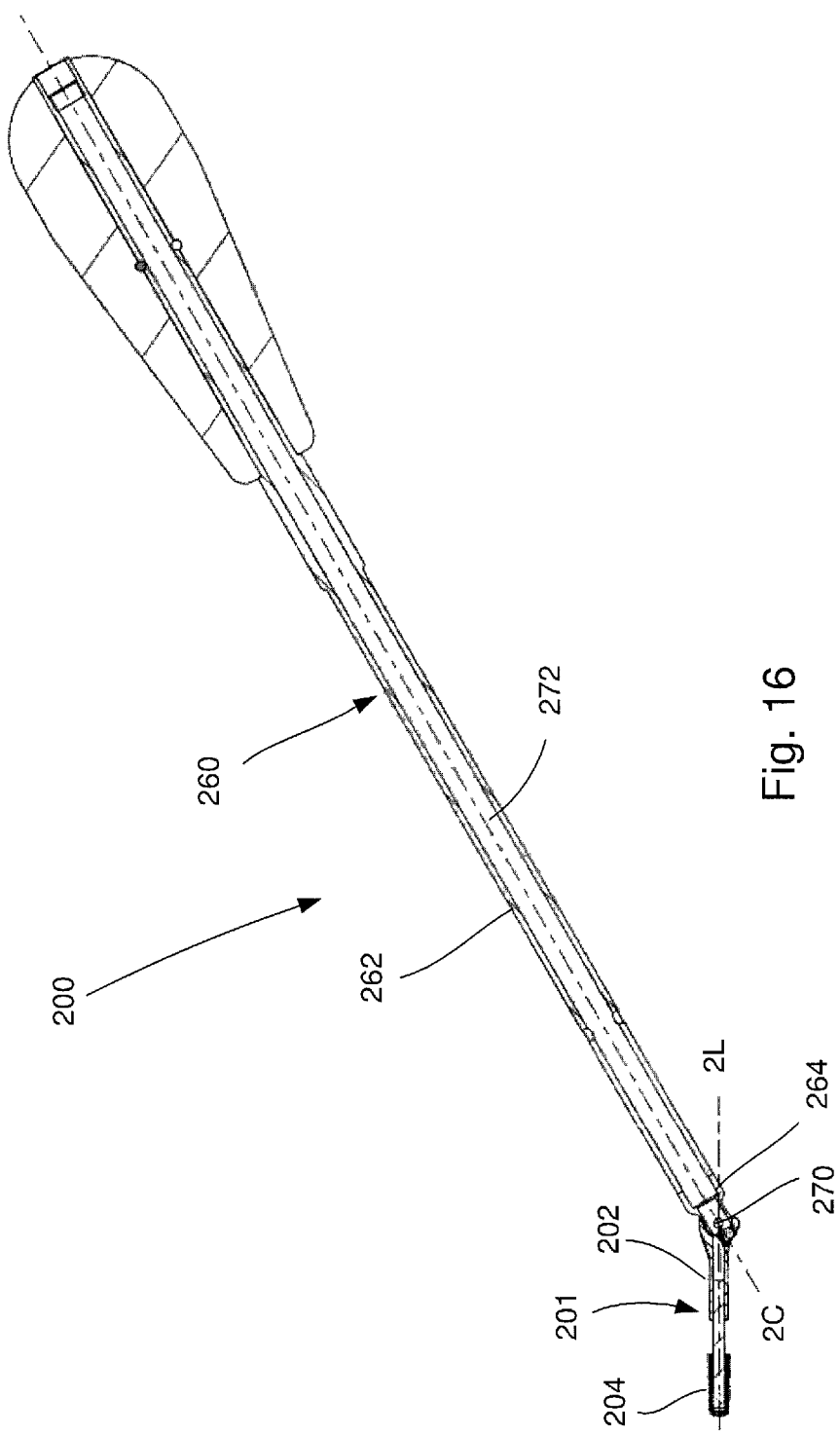
FIG. 16 shows a cross-sectional side view of the driving tool of FIG. 12, in a pivoted configuration.

The driving tool 260, as shown in FIGS. 14-16, is substantially similar to the driving tool 160, comprising an outer sleeve 262 and an inner sleeve 266 receivable within a lumen 272 of the outer sleeve 262. Similarly to the outer sleeve 162, the outer sleeve 262 includes a distal end 264 configured to engage the proximal end 206 of the first element 202. The distal end 264 may include, for example, a pair of protrusions 270 receivable within a corresponding pair of recesses 207 at the proximal end 206 such that the outer sleeve 262 is pivotable with respect to the bone fixation device 201. A distal end 268 of the inner sleeve 266, however, does not engage the proximal end 212 of the second element 204. Since the first and second elements 202, 204 are non-rotatable relative to one another, a driving force applied to the first element 202 transmits a torsional force to the entire bone fixation device 201. Thus, the inner sleeve 266 is receivable within the lumen 272 of the outer sleeve 262 such that the distal end 268 of the inner sleeve 266 contacts the proximal end 212 of the second element 204, holding the second element 204 in a longitudinal position relative to the first element 202 as the bone fixation device 201 is being implanted into the bone. Once the bone fixation device has been driven into the bone, as desired, the inner sleeve 266 may be removed from the driving tool 260 so that the outer sleeve 262 may be pivoted relative to the longitudinal axis 2L of the bone fixation device 201, as shown in FIG. 16, until the lumen 272 is aligned with the central axis of the opening 282. As described above in regard to the system 100, a hole corresponding to the opening 228 may be drilled into the bone via the lumen 272 permitting a bone screw 256 to be inserted therethrough.

As shown in FIGS. 17-18, a bone fixation device 301 according to an alternate embodiment of the present invention may, for example, be substantially similar to the bone fixation device 201. The bone fixation device 301, however, does not include first and second elements longitudinally movable relative to one another. Rather, the bone fixation device 301 comprises an elongated element 302 and a bone engaging member 342. The elongated element 302 extends from a proximal end 306 to a distal end 308 along a longitudinal axis 3L. The proximal end 306 includes a head portion 322 through which an opening 328 extends along a central axis 3C at an angle relative to the longitudinal axis 3L to receive a bone fixation element such as a screw 356 along the central axis 3C. A shaft 326 extending distally from the head portion 322 includes an enlarged proximal portion 320 and an enlarged distal portion 321 connected to one another via a mid portion 346 having a circumference (e.g., diameter) smaller than the enlarged proximal and distal portions 320, 321.

Similarly to the bone engaging member 242, the bone engaging member 342 includes threading 344 along an exterior surface thereof and a channel 316 extending longitudinally therethrough from a closed distal end 352 to an open proximal end 354. The channel 316 is sized and shaped to accommodate the enlarged distal portion 321. The enlarged distal portion 321 of the elongated element 302 is received and fixed within a distal portion of the channel 316 such that the mid portion 346 extends within a proximal portion of the channel 316. Since the mid portion 346 has a smaller diameter than the channel 316, the bone engaging member 342 may deflect relative to the elongated member 302 to provide dynamization to the fractured bone in which the bone fixation device 301 has been implanted. As discussed above in regard to the bone fixation device 201, a range of deflection is determined by a size of the channel 316 relative to a size of the mid portion 346.

The bone fixation device 301 may be implanted into bone in a manner substantially similar to the bone fixation device 202. Specifically, the bone fixation device 301 may be driven into bone via a driving tool substantially similar to the driving tool 260. However, since the elongated element 302 does not move longitudinally relative to the bone engaging member 342, it will be understood by those of skill in the art that an inner sleeve is not required.

Figure 19:
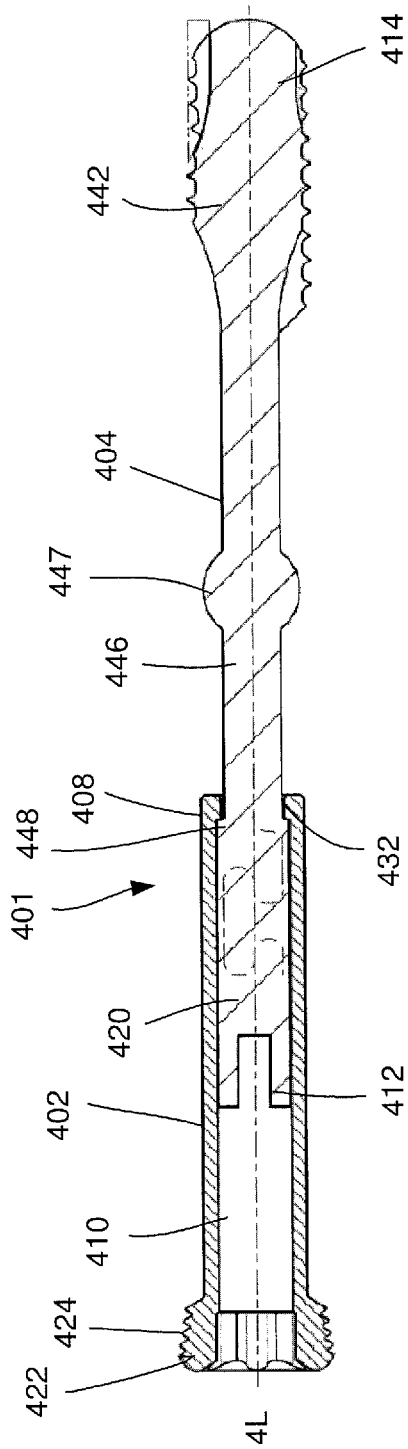
FIG. 19 shows a cross-sectional side view of a device according to a fourth exemplary embodiment of the present invention.
Figure 20:
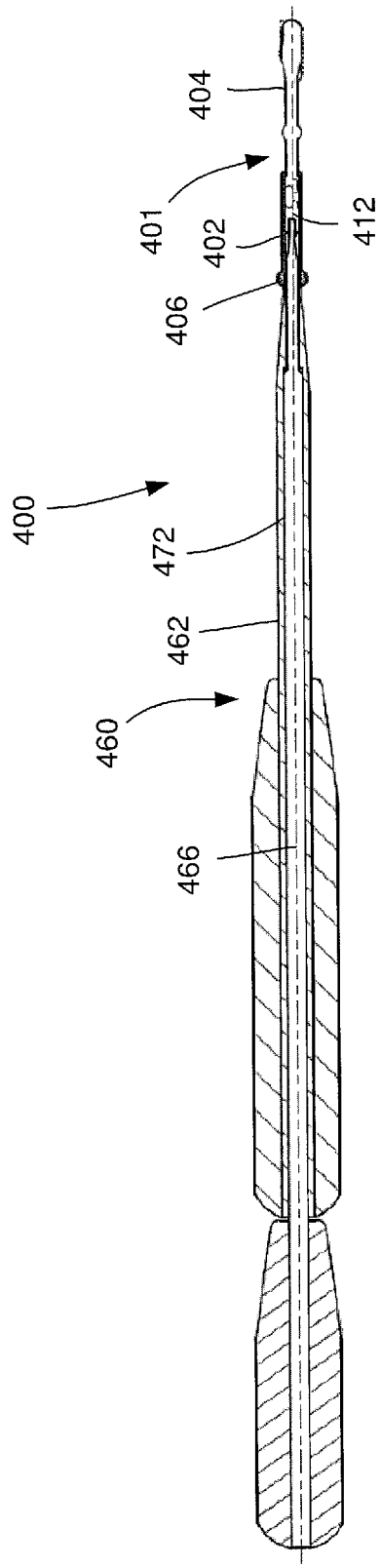
FIG. 20 shows a cross-sectional side view of a driving tool for use with the device of FIG. 19.
Figure 21:
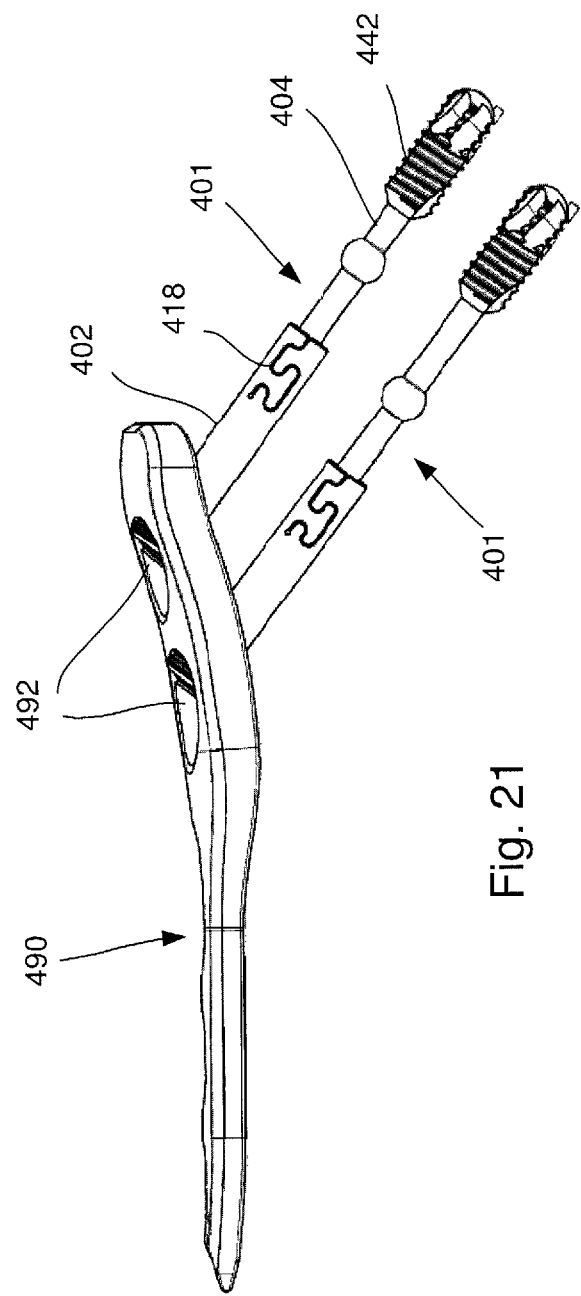
FIG. 21 shows a side view of the device of FIG. 19 inserted through an opening of a bone plate.
Figure 22:
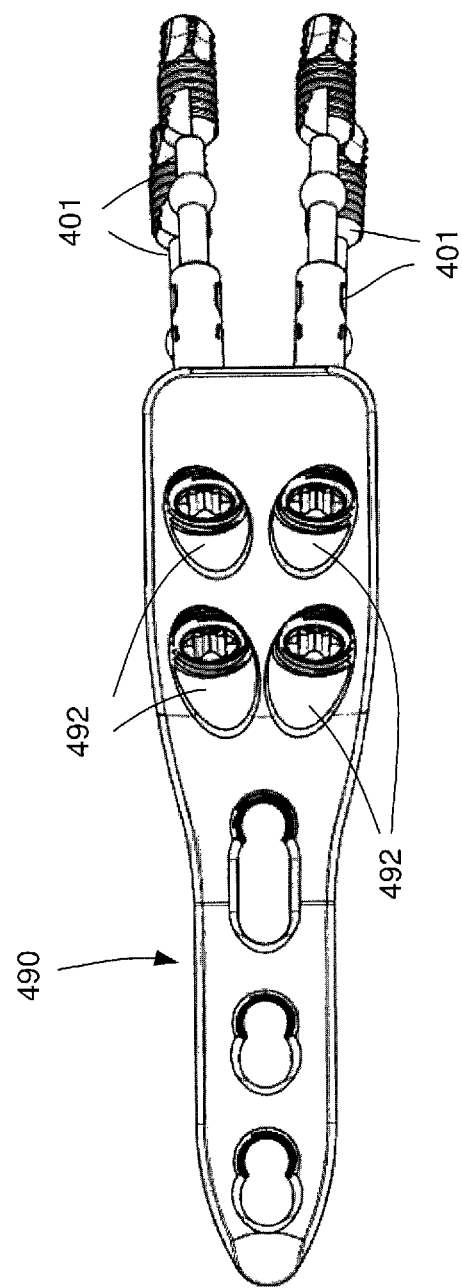
FIG. 22 shows another side view of the device of FIG. 19 of the device and bone plate of FIG. 21.

As shown in FIGS. 19-22, a system 400 according to another exemplary embodiment of the present invention is substantially similar to the system 100, comprising a bone fixation device 401, as shown in FIG. 19, and a driving tool 460, as shown in FIG. 20, for driving the bone fixation device 401 into a bone. As shown in FIGS. 21-22, the bone fixation element 401 may be used with a plate 490 for humeral fractures (or any similar bone fixation member) with the bone fixation element 401 extending through an opening 492 thereof and into a humeral head. The bone fixation device 401 may be substantially similar to the bone fixation device 101 including first and second elements 402, 404, respectively, telescoping relative to one another along a longitudinal axis 4L and rotatable relative to one another about the longitudinal axis 4L. Similarly to the first element 102, the first element 402 extends along the longitudinal axis 4L and includes a channel 410 and a slot 418 extending proximally from a distal end 408 thereof along a portion of a length thereof to permit the distal end 408 to expand to receive an enlarged proximal portion 420 of the second element 404 within the channel 410. The distal end 408 includes a shoulder 432 extending radially inward such that once the enlarged portion 420 has been received therein, the distal end 408 contracts under its natural bias to lock the second element 404 within the channel 410.

Similarly to the second element 104, the second element 404 extends longitudinally from a proximal end 412 to a distal end 414 and includes the enlarged portion 420 along a proximal portion thereof along with a bone engaging structure 442 extending along a distal portion thereof. The bone engaging structure 442 and the enlarged portion 420 may be connected to one another via a mid portion 446 having a cross-sectional area smaller than the enlarged portion 420. The second element 404, however, includes a protrusion 447 extending radially outward from the mid portion 446 such that a limit of proximal motion of second element 404 relative to the first element 402 is defined by contact between the protrusion 447 and the shoulder 432. Thus, a permitted range of motion of the first and second elements 402, 404 relative to one another is defined by a contact between a distal end 448 of the enlarged portion 420 and the shoulder 432 and a contact between the protrusion 447 and the shoulder 432.

As shown in FIG. 20, the driving tool 460 may be substantially similar to the driving tool 160, as described above, comprising an outer sleeve 462 and an inner sleeve 466 receivable within a lumen 472 of the outer sleeve 462. Similarly to the outer sleeve 162, a distal end 464 of the outer sleeve 462 is configured to engage the proximal end 406 of the first element 402 while a distal end 468 of the inner sleeve 466 is configured to engage the proximal end 412 of the second element 402. Thus, the inner sleeve 466 may be used to drive the second element 404 into the bone while the outer sleeve 462 may be used to drive the first element 402 into the bone. In an exemplary embodiment, the first and second elements 402, 404 may be driven into the bone independent of one another.

In one exemplary embodiment, as shown in FIGS. 20-21, the bone fixation element 401 may be used with a humeral plate 490, which includes a plurality of openings 492 extending therethrough along an axis which, when the plate 490 is positioned along the bone, extend into the humeral head. The plate 490 may include, for example, four openings 492 extending therethrough such that four bone fixation elements 401 may be inserted into the humeral head. It will be understood by those of skill in the art, however, that any number of openings 492 and bone fixation elements 491 may be utilized. The bone fixation element 401 may be driven into the bone though the opening 492 using the driving tool 460, until a threading a 424 along a head portion 422 of the first element 402 engages a corresponding threading along an interior of the opening 492. It will be understood by those of skill in the art that the bone fixation element 401 will permit compression of a fracture in the humeral head as the bone heals.

Although the bone fixation elements 101, 201, 401 described above specifically describe assembly of first and second elements via a slot 118, 418 or a pin 218, it will be understood by those of skill in the art that the telescoping assembly between first and second elements may be achieved in a variety of different ways. Thus, the assembly mechanisms described below may be utilized in any of the bone fixation elements 101, 201, 401 described above.

As shown in FIGS. 23-24, a bone fixation device 501 according to another exemplary embodiment is substantially similar to any of the bone fixation devices 101, 201, 301 described above, comprising a first element 502 including a first channel 510 extending therethrough sized and shaped to receive a proximal portion 540 of a second element 504. Similarly to the second elements described above, the second element 504 includes a proximal portion 540 and a distal portion including a bone engaging structure 542. A distal end 508 of the first element includes a shoulder 532 extending radially inward. The proximal portion 540 includes a pair of protrusions 520 diametrically opposed to one another and extending laterally outward from the proximal portion 540. The proximal portion 540 also includes an elongated slot 521 extending laterally therethrough between the opposed protrusions 520. The proximal portion 540 is formed of an elastic material such that the protrusions 520 may be pressed toward one another, as shown in FIG. 23, (e.g., toward a centerline of the second element 504) permitting the protrusions 520 to be passed proximally past the shoulder 532 into the channel 510. Once the protrusions 520 have been received within the channel 510, the proximal portion 540 reverts to its initial configuration under its natural bias, as shown in FIG. 24, while the protrusions 520 are prevented from passing distally past the shoulder 532. Thus, it will be understood by those of skill in the art that distal movement of the second element 504 relative to the first element 502 is limited by contact between the protrusions 520 and a proximal surface of the shoulder 532.

Figure 25:
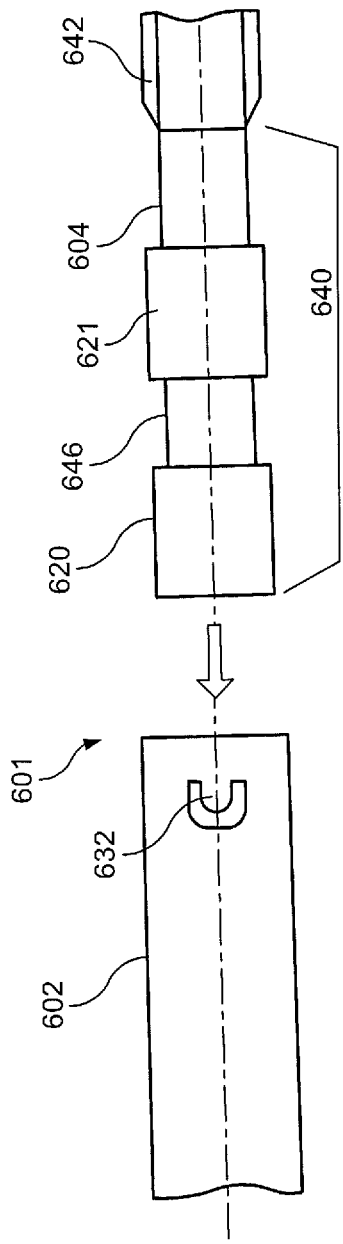
FIG. 25 shows a cross-sectional side view of a portion of a device according to another exemplary embodiment of the present invention, prior to assembly.
Figure 26:
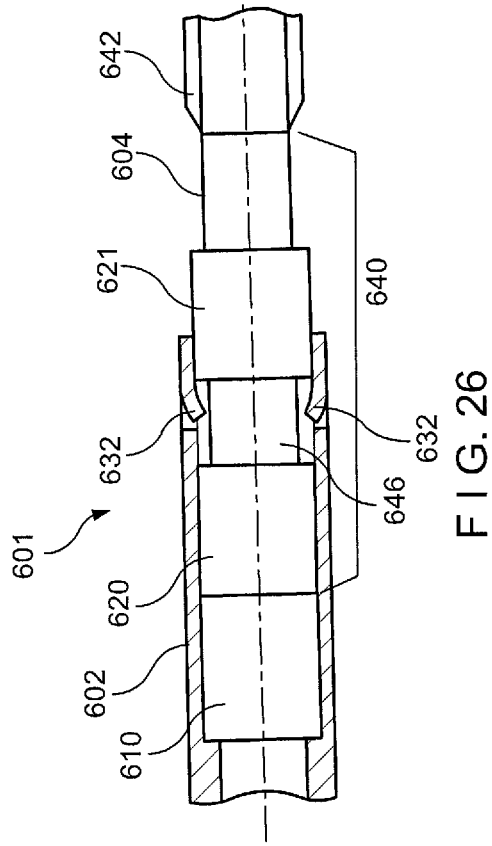
FIG. 26 shows a cross-sectional side view of the device of FIG. 25, in an assembled configuration.

As shown in FIGS. 25-26, a bone fixation device 601 according to another exemplary embodiment may be substantially similar to any of the bone fixation devices 101, 201, 301 described above, comprising a first element 602 with a channel 610 extending therethrough sized and shaped to receive a first enlarged portion 620 at a proximal end 612 of a second element 604. The second element 604 includes a proximal portion 640 including the first enlarged portion 620 at the proximal end 612 and a second enlarged portion 621 distally of the first enlarged portion 620. The first and second enlarged portions 620, 621 are connected to one another via a smaller cross-section portion 646. The second element 604 also includes a distal portion including a bone engaging structure 642.

The first element 602 includes a pair of elastic tabs 632 extending inward toward a centerline of the channel 610 along a distal portion thereof. The pair of tabs 632 in this embodiment are, for example, diametrically opposed to one another. Thus, when the first enlarged portion 620 is moved proximally into the channel 610, the tabs 632 elastically deform away from the centerline of the channel 610 to permit the first enlarged portion to be moved proximally therepast. Once the first enlarged portion 620 has been moved proximally past the tabs 632, the tabs 632 revert to their initial configuration under their natural bias with the tabs 632 extending into the channel 610 so that the first enlarged portion 620 is locked therein. A range of motion between the first and second elements 602, 604 is defined by a length of the smaller cross-section portion 646 (i.e., a distance between the first and second enlarged portions 620, 621).

Figure 27:
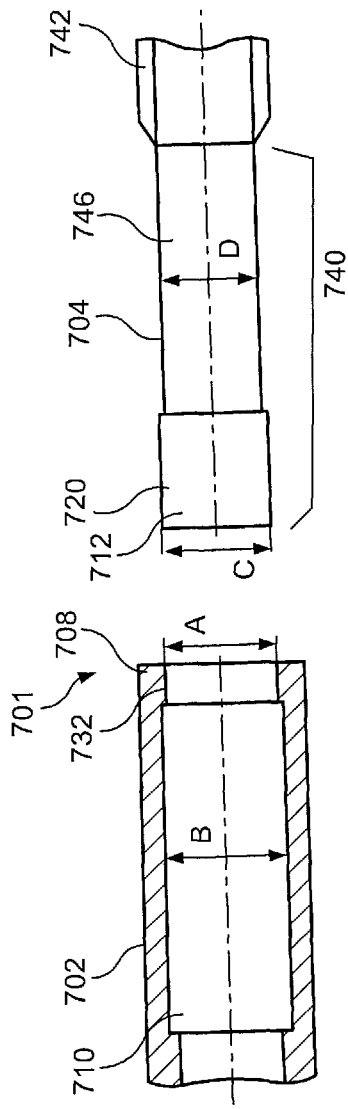
FIG. 27 shows a cross-sectional side view of a portion of a device according to yet another exemplary embodiment of the present invention, prior to assembly.
Figure 28:
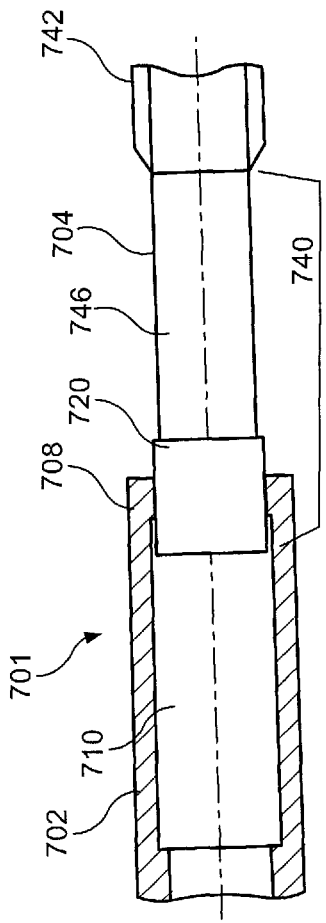
FIG. 28 shows a cross-sectional side view of the device of FIG. 27, in a process of being assembled.
Figure 29:
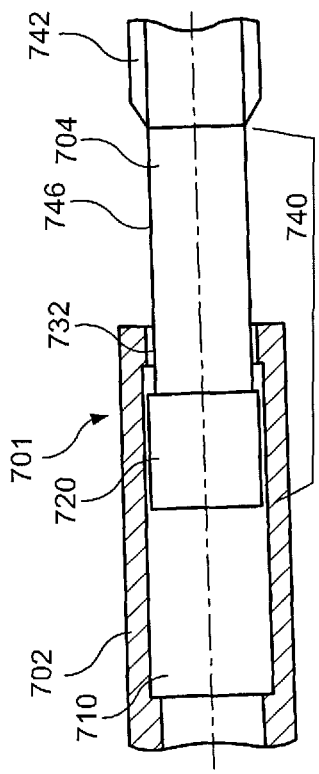
FIG. 29 shows a cross-sectional side view of the device of FIG. 27, in an assembled configuration.

As shown in FIGS. 27-29, a bone fixation device 701 according to another exemplary embodiment of the present invention may be substantially similar to any of the bone fixation devices 101, 201, 401 described above, comprising a first element 702 including a channel 710 extending therethrough sized and shaped for receiving a proximal portion 740 of a second element 704. The proximal portion 740 includes an enlarged portion 720 at a proximal end 712 thereof. The second element 704 also includes a distal portion including a bone engaging structure 742. The first element 702 includes a shoulder 732 extending radially into the channel 710 at a distal end 708 thereof. A cross-sectional area A of the channel 710 formed by the shoulder 732 is substantially similar to a cross-sectional area C of the enlarged portion 720 such that the enlarged portion 720 may be press-fit proximally past the shoulder 732. A cross-sectional area B of the channel 710 proximal to the shoulder 732 is slightly larger than the cross-sectional area C and the cross-sectional area A is slightly larger than a cross-sectional area D of a remaining length 746 of the proximal portion 740 such that once the enlarged portion 720 has been moved proximally past the shoulder 732 into the channel 710, the enlarged portion 720 is permitted to slide longitudinally within the channel 710. Once the first and second elements 702, 704 have been assembled as described above, a large force would be required to disassemble the components as would be understood by those skilled in the art.

Figure 30:
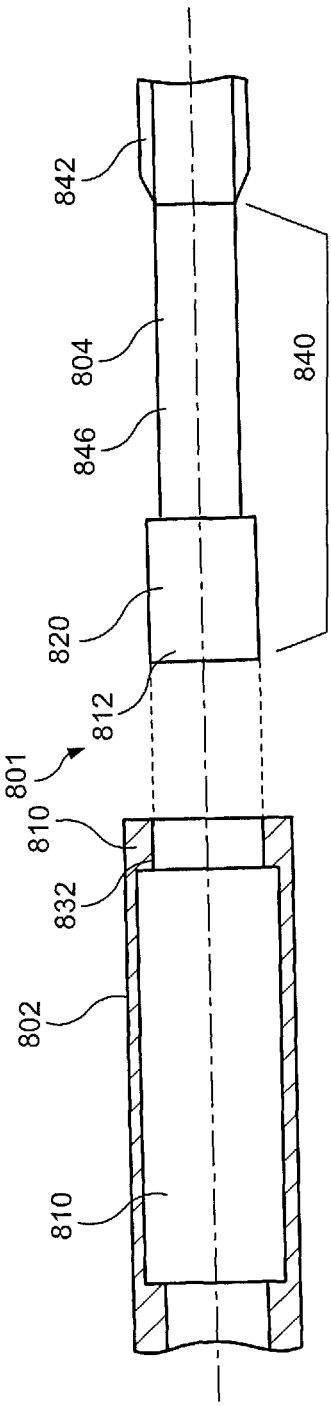
FIG. 30 shows a cross-sectional side view of a portion of a device according to another exemplary embodiment of the present invention, prior to assembly.
Figure 31:
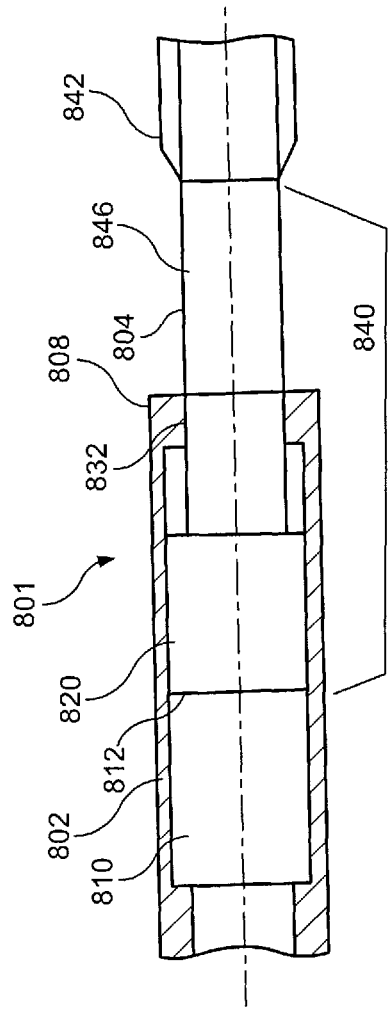
FIG. 31 shows a cross-sectional side view of the device of FIG. 30, in an assembled configuration.

As shown in FIGS. 30-31, a bone fixation device 801 according to another exemplary embodiment may be substantially similar to the bone fixation device 701 described above, comprising a first element 802 including a channel 810 extending therethrough sized and shaped to receive a proximal portion 840 of a second element 804. Similarly to the second element 704, the proximal portion 840 includes an enlarged portion 820 at a proximal end 812 thereof, which has a cross-sectional area larger than that of a remaining length 846 thereof. The second element 804 also includes a distal portion with a bone engaging structure 842 therealong. Similarly to the first element 702, the first element 802 includes a shoulder 832 extending radially into the channel 810 at a distal end 808 thereof, a cross-sectional area of the channel 810 formed by the shoulder 832 being substantially the same as a cross-sectional area of the enlarged portion 820. At least a distal portion of the first element 802, however, is formed of a shape memory material which expands when heat is applied thereto. Thus, when heated, the distal end 808 expands permitting the enlarged portion 820 to be moved proximally therepast into the channel 810. Alternatively or, in addition, at least the enlarged portion 820 of the second element 804 may also be formed of a shape memory material which shrinks when cooled. Thus, when the enlarged portion 820 is cooled, the cross-sectional area of the enlarged portion 820 becomes smaller permitting the enlarged portion 820 to be moved proximally past the shoulder 832 into the channel 810. As would be understood by those skilled in the art, the transition temperatures for these elements are selected so that, once the materials have returned to the ambient temperature in the environment in which they are to be deployed, the distal end 808 of the first element 802 and the enlarged portion 820 of the second element 804 will revert to their original size and shape to lock the enlarged portion 820 within the channel 810.

Figure 32:
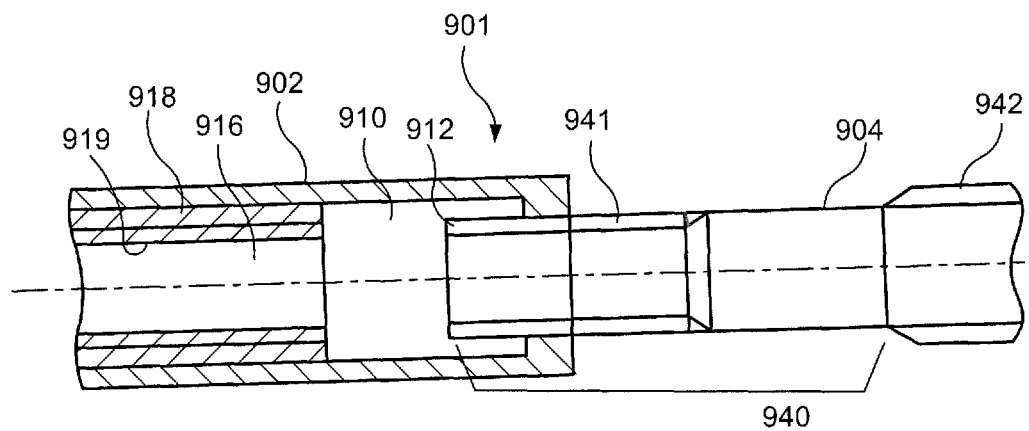
FIG. 32 shows a cross-sectional side view of a device according to yet another exemplary embodiment of the present invention, in a process of being assembled.
Figure 33:
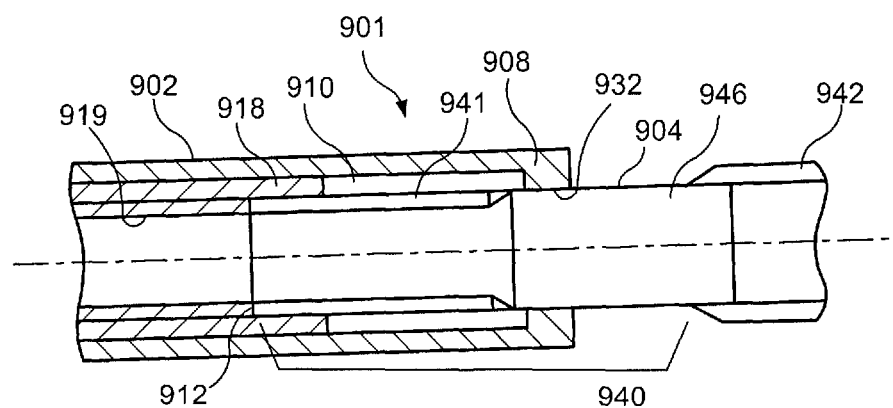
FIG. 33 shows a cross-sectional side view of the device of FIG. 32, in an assembled configuration.

As shown in FIGS. 32-33, a bone fixation device 901 may be substantially similar to any one of the bone fixation devices 101, 201, 401 described above, comprising a first element 902 including a channel 910 extending therethrough sized and shaped to receive a proximal portion 940 of a second element 904. The bone fixation device 901, however, further comprises a sleeve 918 distally insertable through a proximal end of the channel 910 to engage the proximal portion 940 of the second element 904, as will be described in further detail below. The proximal portion 940 is sized and shaped to be passed proximally through a distal end 908 of the first element which includes a shoulder 932 extending radially inward therefrom. The proximal portion 940 includes a first engaging structure 941 such as, for example, a threading extending from a proximal end 912 thereof along a portion thereof.

The sleeve 918 is sized and shaped to be passed through a proximal end of the first element 902 and into the channel 910. The sleeve 918 includes a lumen 916 extending therethrough sized and shaped to receive the proximal end 912 of the second element 904. The lumen 916 includes a second engaging structure 919 (e.g., threading) extending from a distal end 954 thereof along an interior surface thereof for engaging the first engaging structure 941 of the second element 904. Thus, the proximal end 912 of the second element 904 may be inserted proximally past the shoulder 932 while the sleeve 918 is inserted distally through the channel 910 such that the first and second engaging structures 941, 919 engage one another. Once engaged, the proximal end 912 of the second element 904 is prevented from moving distally past the shoulder 932 of the first element 902 such that the first and second elements 902, 904 are permitted to move longitudinally relative to one another within a permitted range of motion.

Figure 34:
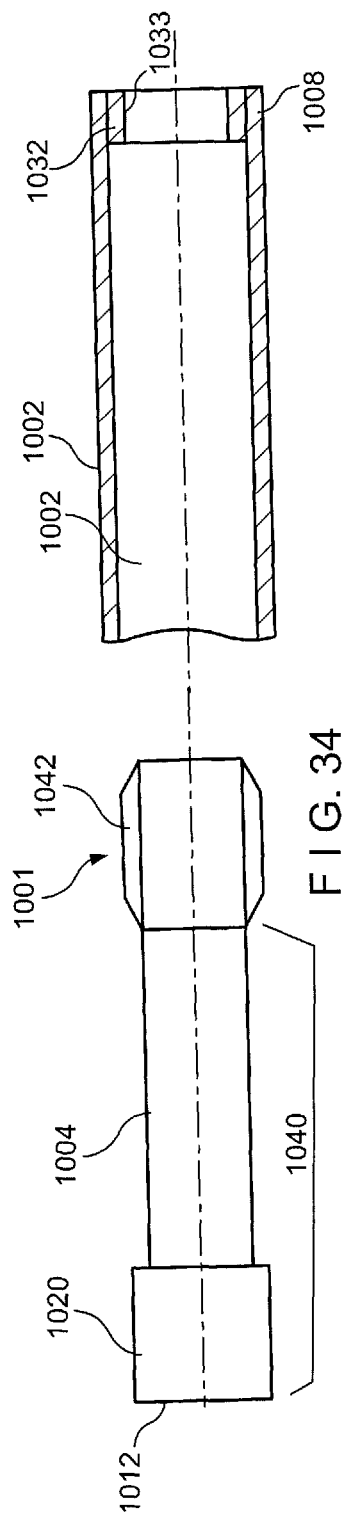
FIG. 34 shows a cross-sectional side view of a portion of a device according to another exemplary embodiment of the present invention, prior to assembly.
Figure 35:
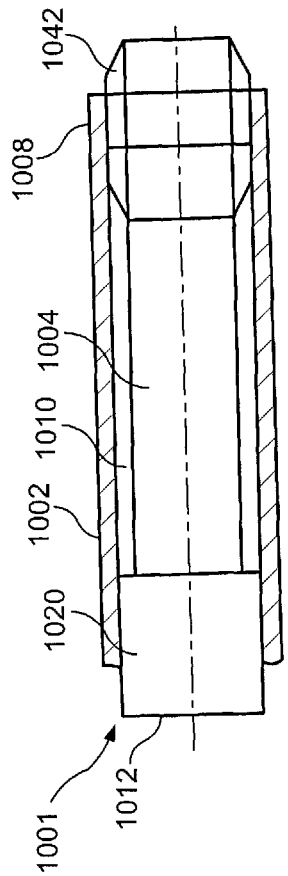
FIG. 35 shows a cross-sectional side view of the device of FIG. 34, in a process of being assembled.
Figure 36:
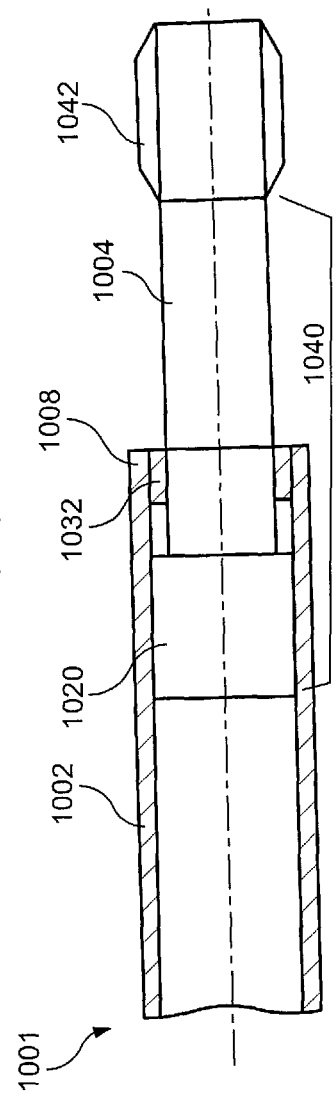
FIG. 36 shows a cross-sectional side view of the device of FIG. 34, in an assembled configuration.

As shown in FIGS. 34-36, a bone fixation device 1001 according to another exemplary embodiment may be substantially similar to any of the bone fixation devices 101, 201, 401 described above, comprising a first element 1002 including a channel 1010 extending therethrough shaped and sized to receive a proximal portion 1040 of a second element 1004. The second element 1004, however, is passed into the channel 1010 via a proximal end of the first element 1002, as will be described in further detail below. The first element 1002 includes a shoulder 1032 extending radially into the channel 1010 at a distal end 1008 thereof. The shoulder 1032 includes an engaging structure 1033 such as, for example, threading, extending therealong. The second element 1004 includes a proximal portion 1040 includes an enlarged portion 1020 at a proximal end 1012 thereof and a distal portion including a bone engaging structure 1042. The bone engaging structure 1042 and the engaging structure 1033 of the shoulder 1032 correspond to one another (e.g., have corresponding threadings) such that when the second element 1004 is inserted distally through the channel 1010, the bone engaging structure 1042 is permitted to move distally past the shoulder 1032 via, for example, a rotation of the second element 1004 relative to the first element 1002. Once the bone engaging structure 1042 has distally passed the shoulder 1032, the second element 1004 is permitted to slide longitudinally relative to the first element 1002. A permitted range of telescoping motion between the first and second elements 1002 is defined by a distance between the enlarged portion 1020 and the bone engaging structure 1042.

As shown in FIGS. 37 and 38, a bone fixation device 1101 may be substantially similar to any of the bone fixation devices 101, 201, 401 described above, comprising a first element 1102 including a channel 1110 extending therethrough sized and shaped to receive a proximal portion 1140 of a second element 1104. The first element 1102, however, does not include a shoulder at a distal end 1108 thereof. The second element 1104 includes an enlarged portion 1120 at a proximal end 1112 end thereof and a non-enlarged portion 1146 extending distally therefrom. The second element 1104 also includes a distal portion including a bone engaging portion 1142. The enlarged portion 1120 and the bone engaging portion 1142 are connected to one another via the non-enlarged portion 1146.

The bone fixation device 1101 further comprises an insert 1118 such as, for example, a ring, slidably mounted over the non-enlarged portion 1146. The insert 1118 is sized and shaped to permit the insert 1118 to slide over the non-enlarged portion 1146 while preventing the insert 1118 from sliding over either the enlarged portion 1120 or the bone engaging structure 1142. The enlarged portion 1120 is inserted proximally into the channel 1110 until the enlarged portion 1120 is received entirely within the channel 1110. The insert 118 is then slid along the non-enlarged portion 1146 until the insert 1118 comes into contact with the distal end 1108 of the first element 1102. The insert 1118 is then attached to the distal end 1108 via, for example, welding. Once the insert 1118 has been attached to the distal end 1108, the enlarged portion 1120 is locked within the channel 1110 and the second element 1104 is longitudinally movable relative to the first element 1102 as the non-enlarged portion 1146 slides through the insert 1118.

As shown in FIGS. 39-40, a bone fixation device 1201 may be substantially similar to any of the bone fixation devices 101, 201, 401 described above, comprising a first element 1202 including a channel 1210 extending therethrough sized and shaped to receive a proximal portion 1240 of a second element 1204. Similarly to the first element 1102 of the bone fixation device 1101, the first element 1202 does not include a shoulder at a distal end 1208 thereof. Rather, the first element 1202 includes a hole 1236 extending laterally therethrough from an exterior thereof to an interior of the channel 1210 along a distal portion thereof. In one exemplary embodiment, the first element 1202 includes a pair of holes 1236 diametrically opposed to one another. It will be understood by those of skill in the art, however, that the first element 1202 may include any number of holes 1236 extending therethrough along any portion about a circumference of the first element 1202. The proximal portion 1240 of the second element 1204 includes a first enlarged portion 1220 at a proximal end 1212 thereof and a second enlarged portion 1221 distally of the first enlarged portion 1220. The first and second enlarged portions 1220, 1221 are connected to one another via a non-enlarged portion 1246. The second element 1204 also includes a distal portion including a bone engaging structure 1242.

The channel 1210 of the first element 1202 is sized and shaped to receive the first and second enlarged portions 1220, 1221. To assemble the bone fixation device 1201, the first enlarged portion 1220 is moved proximally into the channel 1210, past the hole 1236. A pin 1218 is then inserted into each hole 1236, locking the enlarged portion 1220 within the channel 1210. The first and second elements 1202, 1204 are longitudinally movable relative to one another with the pin 1218 acting as a stop preventing the first enlarged portion 1220 from moving distally therepast and the second enlarged portion 1221 from moving proximally therepast. Thus, a permitted range of motion between the first and second elements 1202, 1204 is defined by a length of the non-enlarged portion 1246 connecting the first and second enlarged portions 1220, 1221.

As shown in FIGS. 41-42, a bone fixation device 1301 may be substantially similar to any one of the bone fixation devices 101, 201, 401 described above, comprising a first element 1302 including a channel 1310 extending therethrough sized and shaped to receive a proximal portion 1340 of a second element 1304. The first element 1302 includes a shoulder 1332 at a distal end 1308 thereof extending radially into the channel 1310. The proximal portion 1340 of the second element 1304 is sized and shaped be receivable proximally past the shoulder 1332 and into the channel 310. The proximal portion 1340, however, includes an expansion ring 1320 extending about a portion thereof which, when in an expanded configuration, has a cross-sectional area (e.g., diameter) larger than a cross-sectional area of a remaining portion of the proximal portion 1340. The cross-sectional area of the expansion ring 1320 is also larger than a cross-sectional area of the channel 1310 within the shoulder 1332 (e.g., the diameter at the distal end 1308). When moved proximally into the channel 1310, however, the expansion ring 1320 may be elastically deformed to a compressed configuration (e.g., having a smaller diameter than the diameter at the distal end 1308), as shown in FIG. 41, such that the expansion ring 1320 may be moved proximally past the shoulder 1332. Once the expansion ring 1320 has moved past the shoulder 1332 and into the channel 1310, the expansion ring 1320 reverts to the expanded configuration, as shown in FIG. 42, locking the expansion ring 1320 within the channel 1310. The expansion ring 1320 is prevented from moving to the compressed configuration when moved distally against the shoulder 1332 so that the second element 1304 is longitudinally movable relative to the first element 1302, a distal-most position of the second element 1304 relative to the first element 1302 being limited by contact between the expansion ring 1320 and a proximal surface of the shoulder 1332.

As shown in FIGS. 43-46, a bone fixation device 1401 may be substantially similar to any of the bone fixation devices 101, 201, 401 described above, comprising a first element 1402 including a channel 1410 extending therethrough sized and shaped to receive a proximal portion 1440 of a second element 1404. As shown in FIG. 43, the first element 1402 includes an elastic tab 1418 at a distal end 1408 thereof, the tab 1418 defined by a pair of longitudinal slots 1418 extending from the distal end 1408. The pair of slots 1436 extend substantially parallel to one another along a portion of a length of the first element 1402. The elastic tab 1418 also includes a shoulder 1432 extending laterally into the channel 1410 toward a centerline of the first element 1402. The elastic tab 1418 is biased toward a closed configuration, as shown in FIG. 46, but is elastically deformable, as shown in FIG. 45, to expand the distal end 1408 to permit an enlarged portion 1420 of the proximal portion 1440 of the second element 1404 to be moved proximally past the shoulder 1432 and into the channel 1410.

The proximal portion 1440 of the second element 1404 includes an enlarged portion 1420 at a proximal end 1412 thereof. The enlarged portion 1420 is sized and shaped to be slidably movable within the channel 1410, but is larger than a portion of the channel 1410 within the shoulder 1432, when the tab 1418 is in the closed configuration. A remaining length 1446 of the proximal portion 1440 distal of the enlarged portion 1420 is sized and shaped to be slidably movable within the portion of the channel 1410, when the tab 1418 is in the closed configuration. To assemble the first and second elements 1402, 1404, the elastic tab 1418 is deformed to enlarge the distal end 1408 and permit the enlarged portion 1420 of the second element 1404 to be moved proximally past the shoulder 1432 into the channel 1410. Once the enlarged portion 1420 has been moved proximally past the shoulder 1432, the tab 1418 reverts to its initial configuration under its natural bias, slidably locking the enlarged portion 1420 within the channel 1410.

It will be apparent to those skilled in the art that various modifications and variations can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A bone fixation device, comprising:
a first element extending along a first longitudinal axis from a proximal end to a distal end, the first element including a first channel extending therethrough along the first longitudinal axis; and
a second element extending along a second longitudinal axis from a proximal end to a distal end, the second element including a proximal portion sized and shaped to be received within the first channel such that the first and second longitudinal axes are substantially coaxial and a distal portion including a bone engaging structure, a proximal end of the second element slidably locked within the first channel such that the first and second elements are longitudinally movable relative to one another between a permitted range of motion;
a distal opening of the first channel is movable between a non-expanded configuration and an expanded configuration, a diameter of the distal opening, when in the non-expanded configuration being smaller than an inner diameter of a portion of a the first channel proximal thereto, the first element being biased toward the non-expanded configuration; and
the proximal portion of the second element including an enlarged portion sized and shaped to be slidably received within the portion of the first channel proximal to the distal opening, an outer diameter of the enlarged portion being greater than the diameter of the distal opening in the non-expanded configuration and less than the diameter of the distal opening in the non-expanded configuration, the second element further including a central portion extending distally from the enlarged portion and having an outer diameter less than the diameter of the distal opening; and
the distal opening is movable between the non-expanded and expanded configurations via a slot extending proximally from the distal end, the slot extending along a curve defining first and second interlocking parts shaped to engage one another to limit expansion of the distal opening to a desired extent.

2. The device of claim 1, wherein the distal opening is movable between the non-expanded and expanded configurations via a tab defined by a pair of slots extending proximally from the distal end substantially parallel to one another.

3. The device of claim 1, wherein a distal portion of the first element is formed of a shape memory material such that applying a heat thereto moves the distal opening from the non-expanded to the expanded configuration.

4. The device of claim 3, wherein the enlarged portion of the second element is formed of a shape memory material such that cooling the enlarged portion moves the enlarged portion to a compressed configuration having a diameter smaller than a diameter of the distal opening in the non-expanded configuration.

5. The device of claim 1, wherein the distal opening movable between the non-expanded and expanded configurations via a tab bent into the channel toward a centerline of the first element.

6. The device of claim 1, further comprising a pin extending laterally through the first element and into a smaller diameter portion of the proximal portion of the second element such that a range of permitted motion between the first and second elements is defined by a length of the smaller diameter portion.

7. The device of claim 1, wherein a distal opening of the first channel has a smaller diameter than an inner diameter of a portion of a the first channel proximal thereto.

8. The device of claim 7, wherein a proximal portion of the second element includes a pair of protrusions extending laterally outward therefrom and an elongated slot extending laterally through the proximal portion between the pair of protrusions such that the proximal portion is movable between an expanded configuration and a non-expanded configuration, a distance between radially outermost tips of the protrusions being larger than the diameter of the distal opening but smaller than the diameter of the portion of the first channel proximal thereto in the expanded configuration, and a distance between the radially outermost tips being smaller than the diameter of the distal opening in the non-expanded configuration, the proximal portion being biased in the expanded configuration.

9. The device of claim 7, wherein the proximal portion includes an enlarged portion at a proximal end thereof, the enlarged portion having a diameter that is substantially the same as the diameter of the distal opening and smaller than the diameter of the portion of the channel proximal thereto such that the enlarged portion is press fit through the distal opening and into the first channel, a remaining length of the proximal portion extending distally from the enlarged portion having a diameter smaller than the distal opening.

10. The device of claim 7, further comprising a sleeve insertable through a proximal opening of the first channel, an outer diameter of the sleeve having a diameter larger than the diameter of the distal opening and smaller than the inner diameter of the first channel proximal thereto, the sleeve including a threading along an inner surface thereof to engage a corresponding threading along an exterior of the proximal portion.

11. The device of claim 7, wherein an exterior of the bone engaging structure and the interior of the distal opening include corresponding threadings such that the bone engaging structure is driven distally through the first channel distally past the distal opening, the second element including an elongated portion at a proximal end thereof having a diameter larger than the diameter of the distal opening and smaller than the inner diameter of the portion of the first channel proximal the distal opening such that the enlarged portion is prevented from moving distally past the distal opening.

12. The device of claim 7, wherein the proximal portion of the second element includes an expansion ring about a portion thereof, the expansion ring movable between an expanded configuration in which an outer diameter thereof is larger than the diameter of the distal opening and a non-expanded configuration in which the diameter of the outer diameter thereof is smaller than the diameter of the distal opening, the expansion ring biased in the expanded configuration.

13. The device of claim 1, further comprising a ring attachable to the distal end of the first element, the ring having an inner diameter smaller than an inner diameter of the first channel, wherein the proximal portion of the second element including an enlarged portion sized and shaped to be slidably received within the first channel, an outer diameter of the enlarged portion being greater than the inner diameter of the ring, the second element further including a central portion extending distally from the enlarged portion and having an outer diameter less than the inner diameter of the ring.

14. The device of claim 1, wherein the second element includes a second channel extending therethrough along the second longitudinal axis.

15. The device of claim 1, wherein the bone engaging structure is a threading along a length of a distal portion of the first element.

16. The device of claim 1, wherein the first element includes a head portion at a proximal end thereof.

17. The device of claim 16, wherein the first element includes an opening extending through the head portion along a central axis extending at an acute angle with respect to the first longitudinal axis, the opening being sized and shaped to receive a bone fixation element therein.

18. The device of claim 1, wherein the first element includes a threading along a proximal portion thereof configured to engage a hole of a bone plate through which the first element is to be inserted.

19. A system for treating a bone, comprising:
a bone fixation device, including:
a first element extending along a first longitudinal axis from a proximal end to a distal end, the first element including a first channel extending therethrough along the first longitudinal axis; and
a second element extending along a second longitudinal axis from a proximal end to a distal end, the second element including a proximal portion sized and shaped to be received within the first channel such that the first and second longitudinal axes are substantially coaxial and a distal portion including a bone engaging structure, a proximal end of the second element slidably locked within the first channel such that the first and second elements are longitudinally movable relative to one another between a permitted range of motion; and a driving tool, including:
an outer sleeve extending longitudinally from a proximal end to a distal end and including a lumen extending therethrough, the distal end of the outer sleeve configured to engage the proximal end of the first element to prevent relative rotation therebetween; and
an inner sleeve slidable through the lumen of the outer sleeve and extending longitudinally from a proximal end to a distal end, the distal end of the inner sleeve configured to engage the proximal end of the second element.

20. The system of claim 19, wherein the distal end of the outer sleeve includes a pair of diametrically opposed protrusions extending laterally therefrom, the protrusions sized and shaped to be received within corresponding recesses at the proximal end of the first element such that the outer sleeve is pivotable with respect to the first element.

21. The system of claim 19, wherein the distal end is sized and shaped to be received within a corresponding recess at the proximal end of the second element to prevent relative rotation therebetween.

22. The system of claim 19, wherein the driving tool further includes a locking element for releasably locking the outer and inner sleeves relative to one another.

* * * * *